US006077702A

United States Patent [19]

Madrid et al.

[11] Patent Number: 6,077,702

[45] Date of Patent: Jun. 20, 2000

[54] ENDO β-1,4-GLUCANASE FROM ASPERGILLUS

[75] Inventors: Susan Madrid, Vedbaek; Preben Rasmussen, Lyngby; Anita Baruch, Glostrup, all of Denmark

[73] Assignee: Danisco A/S, Copenhagen, Denmark

[21] Appl. No.: 08/913,264

[22] PCT Filed: Mar. 11, 1996

[86] PCT No.: PCT/EP96/01008

§ 371 Date: Apr. 6, 1998

§ 102(e) Date: Apr. 6, 1998

[87] PCT Pub. No.: WO96/29415

PCT Pub. Date: Sep. 26, 1996

[30] Foreign Application Priority Data

Mar. 17, 1995 [GB] United Kingdom .................... 9505475

[51] Int. Cl.[7] ............................... C12N 9/42; C12N 9/14; D21C 1/00; C13J 7/00

[52] U.S. Cl. .......................... 435/209; 435/195; 435/277; 435/320.1; 435/276; 536/23.2

[58] Field of Search .................................... 435/209, 195, 435/277, 276, 320.1; 536/23.2

[56] References Cited

FOREIGN PATENT DOCUMENTS 0458162 11/1991 European Pat. Off. .

OTHER PUBLICATIONS

Okada et al., Agric. Biol. Chem., 49(5), 1257–1265, Feb. 1985.

Sakamoto et al., DDBJ Database, Accession No. D12901, Aug. 1992.

Dalboge et al., geseq 32 Database, Accession No., Q43452, Oct. 1993.

Ooi et al., Swiss–prot 35 Database, Accession No. p22669, Aug. 1991.

*Primary Examiner*—Rebecca E. Prouty
*Assistant Examiner*—M. Monshipouri
*Attorney, Agent, or Firm*—Frommer Lawrence & Haug; Thomas J. Kowalski

[57] ABSTRACT

A glucanase enzyme is described. In addition, there is described a nucleotide sequence coding for the glucanase enzyme and a promoter for controlling its expression.

16 Claims, 31 Drawing Sheets

AMY 637 PROMOTER
SEQUENCE TYPE: Nucleotide
MOLECULE TYPE: DNA
ORIGINAL SOURCE: *Solanum Tuberosum*
SEQUENCE LENGTH: 2094
SEQUENCE:

```
        10         20         30         40
ATTAAGGGGA GCATAAGTGC AGCTCAGAAA TTCACACCTG
        50         60         70         80
ATATTTTCCC AAAGCCCTCA AAAATGTGAA CAAATCTGCT
        90        100        110        120
AAAATGTCAG TCAGAAGGAC TGTTCTTTTA GGTTTTCTTC
       130        140        150        160
TCTCGAGTCA CGAAATCAGA TAATATGATA AGAAATTATG
       170        180        190        200
GAGGATTTAT AATGTATCTG TCTGTTCTTA GGTATAATTA
       210        220        230        240
TGTGTTCCTT TATGATGTAG TAATGGAATT CTGGGCTTAT
       250        260        270        280
ATTAAAGGAA CTGAATATAA ATGTTCGCAT TTTAACTGCG
       290        300        310        320
GAGACTTCGA GTTAGAGCCT TATAATTATG TCTTATCATT
       330        340        350        360
TTATACTGAG ATCATATTAC AGATGATGAA AGCTGACATT
       370        380        390        400
GCATTAGTTA TTCTGTTTTA TACAAGTCAT GTAACTGCTG
       410        420        430        440
CTTGTGAGTT GTGACTGTAA GATAAATTGA TTCAGCCTTC
       450        460        470        480
TGTGGCATTA GCGGAGATCT GATTATACTC TCATCGTCTT
       490        500        510        520
ATCTAAGTTG CTCATGCAAC TTTGTCCTTG ATAGTTGGCT
       530        540        550        560
AATACTACAA CTGGAATTAA GTGTAGTTAT TCGAAATCTC
       570        580        590        600
TGTTGGAAGT TGCTAAGTGC TTAAGTGCTG GTTATTGTAA
       610        620        630        640
ACCCCATCCG AGTTATTATA CAGCATCTGG CTGATGAAAT
       650        660        670        680
GCTGCTCATT TGCAATGGTG ACATAACCAA ATGTTAGTAA
       690        700        710        720
AACATACTAG CTGGTTGAAT GTTAGATGAT TGTTCAACGT
       730        740        750        760
TACATCTCAC AGAAACCTTA TTATGGATTG ACATGTTAGT
       770        780        790        800
TGATCCGAAA GATCCTTCTT TTAAATGCCA AAGCTTGTTA
       810        820        830        840
CAGATTTGAG GAGTTCTTTT ACTTTCTTTT GTTATATCTA
       850        860        870        880
TTTCCCATTC ATTTTGACGT TCAGCCTCAC AGATGTTGTC
       890        900        910        920
ATACTTAGAA ATGTGCGTAT ATATATAGAG AGAGAGAGAT
       930        940        950        960
AGAGTGAAAT GATTATATAG TCGAAGATTA CGAAACTTGA
```

FIG. 1(I)

```
       970        980        990       1000
CATTGAGACA TCTGTGATTG TTTGAAATTT ATGTATATAT
      1010       1020       1030       1040
CTGTAGCATT AGAAACTATA AGAGTTGTTA GCTTCACTTG
      1050       1060       1070       1080
TCTTATTGTT GTGCTCAAAG CAACTTCATC ATACAGTATG
      1090       1100       1110       1120
GTTTTTATAT GCTCTTCCAT TATCACCGAA CCTTATGATT
      1130       1140       1150       1160
ATGTGTACGA GCTTATAATA TTACTGATGG TGATTCAGTA
      1170       1180       1190       1200
TTATGATTAT GTCCTCCATT AATTATTCTG TTTCATACAA
      1210       1220       1230       1240
GTCGTGTAAT TTGCTGTTTG TGATTGTACG ATAAATTGAT
      1250       1260       1270       1280
TCAACCTTCT GCGGTGTTGG TTGAAGTTCA AGTAAATTAG
      1290       1300       1310       1320
CTTTATTTAT CATAGTAGCA TTTGATTATT GATGCTCTGT
      1330       1340       1350       1360
AGCTAATGAT AAGCCATTGA AGGGAAGCAG AAATGGTAAA
      1370       1380       1390       1400
GCTTTCTAAA ATGAATCTAC GAATGGATGA TAAAGTTAAT
      1410       1420       1430       1440
GAATATTGTT GATACTTCTG CAATCAGATT ATGAGTTACT
      1450       1460       1470       1480
GAGTCTACTG TTTTTTAAGC CTGTTTCAGA TGATCGATCA
      1490       1500       1510       1520
TCAACAACAA CATATTCAGT GTAGTAGACA TGATCGATCA
      1530       1540       1550       1560
CTTTCTAATT TTCGATTATG CACCCTCTTT TCTCCAATTT
      1570       1580       1590       1600
GGTCGTCTTC TTTTTTTCAT GATGTCACTG AATTATTCTC
      1610       1620       1630       1640
TGGTCGTCCC CACCATTCAG GAAGTCACTT CGAGCATAAT
      1650       1660       1670       1680
GTGAAAACAT CCACATTTTT CAAATCCAGC AGAATTTTCA
      1690       1700       1710       1720
TCAAACGGGG TTCAACATTT ACTACATGTA TACACTCTGA
      1730       1740       1750       1760
AGTCTGAATC CACTAATTCT AGATGGTGCA TCTGTGCCCC
      1770       1780       1790       1800
CACACTTGTG AAAGCTTATT CTCAATTTTT TATTTTCCAA
      1810       1820       1830       1840
CAACTTGAAT TCAGACCACA CAACTCCCGT GTCTTGTACG
      1850       1860       1870       1880
GTCAGCATCT GAGTGGAGAA CTCAATTAAG TGACTTTAAC
      1890       1900       1910       1920
GTCGAGTTCT ATAGTAAACA ACCCCTATAT CTTTTTTCAA
      1930       1940       1950       1960
GCATGTTAAG ATTGCGAACA CACTGAAATT TCCAGGTCGT
      1970       1980       1990       2000
TAATCTTGTA CCCAGTGTGT GTACTTTTAA AAAAAAAAGT
      2010       2020       2030       2040
CAGTTTTTTA GTCTCTAAAA CACATTTAAA TAGAGTTTAT
      2050       2060       2070       2080
TTGCCATCTT TTGTTCCTCA TACTAGACTT CGGAGTCAAC
      2090
ACAACACAAC AACA
```

FIG. 1(II)

AMY 351 PROMOTER
SEQUENCE TYPE: Nucleotide
MOLECULE TYPE: DNA (genomic)
ORIGINAL SOURCE: *Solanum tuberosum*
SEQUENCE LENGTH: 1734 bp
STRANDEDNESS: Double
TOPOLOGY: Linear
SEQUENCE:

```
        10         20         30         40
TCTTTAAGTT GTTTGCTTGA TTTTTCTTCT TCAATCTTCT
        50         60         70         80
ATATTTAATT CGTTTTAGCT TCAAACTTCT TCAATTTTAT
        90        100        110        120
TTCAATTTAA TTCTACAAAA AAAATCTCTA TTTAGCACCA
       130        140        150        160
TTCATAAAAT TCATGCTCAA AATGGGCAAA CATAAATAAT
       170        180        190        200
AAATGTGAAG TAAATAATGG ATTAAAATAT ATATTTTTGG
       210        220        230        240
GCCTCACATC AACCTTCATA ATTCTTGAAT GAATGAATGA
       250        260        270        280
TAGACTTCAT AATTTTTTAA CCTATACATA TAAGAAAATT
       290        300        310        320
GAGAGTAACT CAAATAACAA GTTGTAGTAT CACATCTTTA
       330        340        350        360
CTATTTGATA ACATTATGAA GGTGATTATA CATTACGTAA
       370        380        390        400
CATTTCTTTT AAAAATATGT AAGCAAATTT ACTTTTTAAC
       410        420        430        440
TTATCATTGA TCTTCATGGT TTTGTCATAA ATCTCAAAGT
       450        460        470        480
TATCATATTT TATATAGCTA TTTGAAAGTA ATTTTATTTT
       490        500        510        520
TACTCATCAT TGAGTGATGC TTTTATTATA ATACTAGTAA
       530        540        550        560
GTTTTATTTA TTATTTTCTT TTAGGGGTGA ATTGTATAAT
       570        580        590        600
ATAATAAAAA ATATATTTTT AGAAATAATG ATTCTTTTAT
       610        620        630        640
TATTAAAAAG TTAAGATATT AGATTATTTA TGCTTGTATA
       650        660        670        680
ATAATGAACG AAGTTTTATT TTCTATGAGT TTCATTAATC
       690        700        710        720
ATGTTTGTAA TTATTTCAAA TTTTGATGTA TTTTTATAAT
       730        740        750        760
TTTGTATTAT TATATTATTA TACTATATTT AAAAATTTAA
       770        780        790        800
AGATCCATAG GGCTTACGCC CCACGTCAAG AGGCTTGCGC
       810        820        830        840
CTTTCCCTAA ATTAAGTAAA ACTCTTCGCC TCATGCCTTA
       850        860        870        880
CGCCTCCGCC TTTTAAAACA CTGATTCCTT TCCTCATATA
       890        900        910        920
GCTTGAGGCG AAAATATTTA ATAAAAACAC TTCTTAATTT
       930        940        950        960
GTTTATATGT TCAATTGAAC ATGTCCGTGA TTAGAAAATT
```

FIG. 2(I)

```
       970        980        990       1000
AAATTAAATT CAATGACAAA TTTAATAATT TGACACAAAA
      1010       1020       1030       1040
TTTATGAAAA AAATATCAAA ATATAAAGAA ATATTTTTTT
      1050       1060       1070       1080
TGAAATGGAT TAAAAAGAAA AAAAAAACAA ATAAATTGAA
      1090       1100       1110       1120
CCGGGATAAG TTGGTTGTTT AATTGATTAT TGATTATGAT
      1130       1140       1150       1160
CTCAATTTGA CATTTTGCGC GATCTTTCGA CCTCAATTCG
      1170       1180       1190       1200
TATGAACTGA CACTACGCCA ATGGACAGTC GCCGTCGTCA
      1210       1220       1230       1240
CCGCCACCGC ACTATTCTCG ACGCGTCGTC TATCTCCTCC
      1250       1260       1270       1280
ACCCCACAGC CGTCAATTCC AAGCTTCCAA TGAACCGTTG
      1290       1300       1310       1320
CCATGTGTCA CTGCCTATTC ACCGCGAAAC ATGAATATCA
      1330       1340       1350       1360
CTGACGAACG ATTTCGGAGC GGAACGAATC CAGAAAATGG
      1370       1380       1390       1400
ATTACTTTCT ATAAATTCCT CGAATCTCAA CTCCATTTCG
      1410       1420       1430       1440
TAAAAATAAA ATTAAAAATA TTGTTTCTTT TTGTATTTCT
      1450       1460       1470       1480
TTTTGTATTT CTGGTTTATG TGGTGATCGA ATTTTCAATT
      1490       1500       1510       1520
TTTTTACTGG TAGTGATTCC TACTTTTCTT CAATTGCATT
      1530       1540       1550       1560
TCTCCTTTTT CCATTTCACG GTTGAGAATT CATGATTCCT
      1570       1580       1590       1600
TATCAGAGGA ATCGATCCGA TTTGACTAAT TTCACTTTTC
      1610       1620       1630       1640
GTCTGTATAA ATACCAGAGT ATCTAGGTTG AGGAACGTAA
      1650       1660       1670       1680
TTTCAAGCTG CGATCGGCTT TTTCCCCTGA ACGAGCAAAC
      1690       1700       1710       1720
ACAGGTTGTG GGTTCGAGTT AGCAAGGGAC GTATAATCTC
      1730
AACTACAATC CATT
```

FIG. 2(II)

α-AMYLASE CODING SEQUENCE
(i) SEQUENCE CHARACTERISTICS:
(A) LENGTH: 2017 base pairs
(B) TYPE: nucleic acid
(C) STRANDEDNESS: double
(D) TOPOLOGY: linear
(A) LENGTH: 475 amino acids
(B) TYPE: amino acid
(C) STRANDEDNESS: single
(D) TOPOLOGY: linear

```
ATG AAG TCT CTC GCC GCA ATT GCT GCT CTG CTG TCG CCC ACA CTG GTC       48
Met Lys Ser Leu Ala Ala Ile Ala Ala Leu Leu Ser Pro Thr Leu Val
-18         -15                 -10                     -5

CGG GCA GCG ACT CCG GAT GAG TGG AAA GCT CAG TCG ATC TAT TTC ATG       96
Arg Ala Ala Thr Pro Asp Glu Trp Lys Ala Gln Ser Ile Tyr Phe Met
         1               5                  10

CTG ACG GAC CGG TTT GCG CGT ACC GAC AAT TCG ACC ACG GCT CCC TGT      144
Leu Thr Asp Arg Phe Ala Arg Thr Asp Asn Ser Thr Thr Ala Pro Cys
 15                 20                  25                  30

GAC ACC ACT GCC GGG GTATGCAACT AACCCTGTGT TTCTCTTCCC GGGACGTACA      199
Asp Thr Thr Ala Gly
                 35

AGGGGTCTTC TCCATGCTAA CCGTGCACAT GCAG AAA TAT TGC GGG GGA ACA        251
                                      Lys Tyr Cys Gly Gly Thr
                                                       40

TGG CGA GGT ATC ATC AAC AAC GTAAGTGGCT TCTGATTTTC GCTCAATAAT         302
Trp Arg Gly Ile Ile Asn Asn
             45

CTTCGTCGCG TGACTTTATT TCCTAG CTG GAT TAC ATC CAG GAT ATG GGC TTC     355
                             Leu Asp Tyr Ile Gln Asp Met Gly Phe
                                  50                  55

ACA GCT ATC TGG ATA ACT CCA GTG ACA GCC CAG TGG GAC GAC GAT GTG      403
uThr Ala Ile Trp Ile Thr Pro Val Thr Ala Gln Trp Asp Asp Asp Val
         60                  65                  70

GAT GCG GCA GAT GCA ACG TCG TAT CAC GGT TAT TGG CAG AAA GAC  CT      450
Asp Ala Ala Asp Ala Thr Ser Tyr His Gly Tyr Trp Gln Lys Asp  Leu
     75                  80                  85

GTGCGCAACC CTGCTCCATG GATCGCTGGC TGCAAACTCG TGCTGATCGG TGATTTTTTT    510

TTTTTTTTTT TTGAAACAG A TAC TCT CTG AAT TCG AAA TTC GGC ACT GCC       560
                       Tyr Ser Leu Asn Ser Lys Phe Gly Thr Ala
                        90                  95
```

FIG. 3(I)

```
GAT GAC TTG AAA GCC CTG GCT GAT GCC CTT CAC GCC CGT GGG ATG CTT     608
Asp Asp Leu Lys Ala Leu Ala Asp Ala Leu His Ala Arg Gly Met Leu
100                 105                 110                 115

CTC ATG GTC GAC GTC GTG GCT AAT CAC TTT GTACGGACCA TCTACATACC       658
Leu Met Val Asp Val Val Ala Asn His Phe
                120                 125

TGGGAAACGC GAAGAAGGAA AAAAAAAAAA AGGCGCACGC TAACATTTCG CGTTTAG      715

GGC TAC GGC GGT TCT CAT AGC GAG GTG GAT TAC TCG ATC TTC AAT CCT     763
Gly Tyr Gly Gly Ser His Ser Glu Val Asp Tyr Ser Ile Phe Asn Pro
                130                 135                 140

CTG AAC AGC CAG GAT TAC TTC CAC CCG TTC TGT CTC ATT GAG GAC TAC     811
Leu Asn Ser Gln Asp Tyr Phe His Pro Phe Cys Leu Ile Glu Asp Tyr
            145                 150                 155

GAC AAC CAG GAA GAA GTC GAA CAA TGC TGG CTG GCC GAT ACT CCG ACG     859
Asp Asn Gln Glu Glu Val Glu Gln Cys Trp Leu Ala Asp Thr Pro Thr
        160                 165                 170

ACA TTG CCC GAC GTG GAC ACC ACC AAT CCT CAG GTT CGG ACG TTT TTC     907
Thr Leu Pro Asp Val Asp Thr Thr Asn Pro Gln Val Arg Thr Phe Phe
    175                 180                 185

AAC GAC TGG ATC AAG AGC CTG GTG GCG AAC TAC TCC  A GTATGATTGT       954
Asn Asp Trp Ile Lys Ser Leu Val Ala Asn Tyr Ser
190                 195                 200

TCCCGCGGTA ACGCTTTAGG GCTTGCTCTA ACTGAAATCG ACAG  TC GAT GGT CTG   1009
                                                 Ile Asp Gly Leu
                                                             205

CGC GTC GAC ACC GTT AAG CAC GTG GAG AAA GAT TTC TGG CCC GAC TTC    1057
Arg Val Asp Thr Val Lys His Val Glu Lys Asp Phe Trp Pro Asp Phe
                210                 215                 220

AAC GAA GCT GCT GCG TGT ACC GTC GGC GAG GTG TTC AAC GGT GAC CCA    1105
Asn Glu Ala Ala Ala Cys Thr Val Gly Glu Val Phe Asn Gly Asp Pro
            225                 230                 235

GCG TAC ACC TGC CCA TAC CAG GAA GTG CTG GAT GGC GTT CTG AAC TAT    1153
Ala Tyr Thr Cys Pro Tyr Gln Glu Val Leu Asp Gly Val Leu Asn Tyr
        240                 245                 250

CCG  AT  GTGAGTGATT CCGAAAGTTC CATCGATCAG GCTTTCTGAC GCATGAGAAC    1208
Pro  Ile
     255
```

FIG. 3(II)

```
AGC TAC TAT CCT GCG CTT GAT GCA TTC AAG TCT GTC GGC GGC AAT CTC    1256
    Tyr Tyr Pro Ala Leu Asp Ala Phe Lys Ser Val Gly Gly Asn Leu
                260                 265                 270

GGC GGC TTG GCT CAG GCC ATC ACC ACC GTG CAG GAG AGC TGC AAG GAT    1304
Gly Gly Leu Ala Gln Ala Ile Thr Thr Val Gln Glu Ser Cys Lys Asp
            275                 280                 285

TCC AAT CTG CTC GGC AAT TTC CTT GAG AAT CAC GAC ATT GCT CGC TTT    1352
Ser Asn Leu Leu Gly Asn Phe Leu Glu Asn His Asp Ile Ala Arg Phe
        290                 295                 300

GCT  TC  GTATGGACAC TCTTTTTGAA GCCCTCATCG ATTGGGGATG CTGACACGGA    1407
Ala  Ser

CAACAACAAC AG G TAC ACG GAT GAC CTT GCT CTC GCC AAG AAT GGT CTC    1456
                Tyr Thr Asp Asp Leu Ala Leu Ala Lys Asn Gly Leu
                305                 310                 315

GCT TTC ATC ATC CTC TCG GAT GGT ATT CCG ATC ATC TAC ACG GGC CAG    1504
Ala Phe Ile Ile Leu Ser Asp Gly Ile Pro Ile Ile Tyr Thr Gly Gln
            320                 325                 330

GAG CAG CAC TAC GCC GGT GAT CAC GAT CCC ACA AAT CGT GAG GCC GTC    1552
Glu Gln His Tyr Ala Gly Asp His Asp Pro Thr Asn Arg Glu Ala Val
        335                 340                 345

TGG CTG TCT GGC TAC AAT ACC GAC GCC GAG CTG TAC CAG TTC ATC AAG    1600
Trp Leu Ser Gly Tyr Asn Thr Asp Ala Glu Leu Tyr Gln Phe Ile Lys
    350                 355                 360

AAG GCC AAT GGC ATC CGC AAC TTG GCT ATC AGC CAG AAC CCG GAA TTC    1648
Lys Ala Asn Gly Ile Arg Asn Leu Ala Ile Ser Gln Asn Pro Glu Phe
365                 370                 375                 380

ACC TCC TCC AAG GTGAGTACAA TAACAAACTT TTCGAAAAAT TTTTCACCGG        1700
Thr Ser Ser Lys

AGAAAACCTA AGATTCGGCT AACAAAACAA AAAAAAAAAA G ACC AAG GTC ATC      1753
                                              Thr Lys Val Ile
                                              385

TAC CAA GAC GAT TCG ACC CTT GCC ATT AAC CGG GGC GGC GTC GTT ACT    1801
Tyr Gln Asp Asp Ser Thr Leu Ala Ile Asn Arg Gly Gly Val Val Thr
    390                 395                 400

GTC CTG AGC AAT GAA GGC GCC TCC GGG GAG ACC GGG ACT GTC TCC ATT    1849
Val Leu Ser Asn Glu Gly Ala Ser Gly Glu Thr Gly Thr Val Ser Ile
405                 410                 415                 420
```

FIG. 3(III)

```
CCG GGA ACT GGC TTC GAG GCC GGC ACG GAA TTG ACT GAT GTC ATC TCC     1897
Pro Gly Thr Gly Phe Glu Ala Gly Thr Glu Leu Thr Asp Val Ile Ser
                425                 430                 435

TGC AAG ACC GTG ACT GCG GGG GAC AGC GGG GCG GTC GAC GTG CCC TTG     1945
Cys Lys Thr Val Thr Ala Gly Asp Ser Gly Ala Val Asp Val Pro Leu
            440                 445                 450

TCG GGC GGA CTG CCA AGC GTG CTC TAT CCC AGC TCC CAG CTG GCC AAG     1993
Ser Gly Gly Leu Pro Ser Val Leu Tyr Pro Ser Ser Gln Leu Ala Lys
        455                 460                 465

AGT GGT CTG TGT GCG TCG GCG TGA                                     2017
Ser Gly Leu Cys Ala Ser Ala
    470                 475
```

FIG. 3(IV)

α-AMYLASE CODING SEQUENCE
SEQUENCE TYPE: Nucleotide
MOLECULE TYPE: DNA
ORIGINAL SOURCE: *Solanum Tuberosum*
SEQUENCE LENGTH: 1570
SEQUENCE:

| 10 | 20 | 30 | 40 |
|---|---|---|---|
| TGTGGTGATC | GAATTTTCAA | TTTTTTTACT | GAGTATCTAG |
| 50 | 60 | 70 | 80 |
| GTTGAGGAAC | GTAATTTCAA | GCTGCGATCG | GCTTTTTCCC |
| 90 | 100 | 110 | 120 |
| CTGAACGAGC | AAACACAGGT | TGTGGGTTCG | AGTTAGCAAG |
| 130 | 140 | 150 | 160 |
| GGACGTATAA | TCTCAACTAC | AATCCATTAT | GGCGCTTGAT |
| 170 | 180 | 190 | 200 |
| GAAAGTCAGC | AGTCTGATCC | ATTGGTTGTG | ATACGCAATG |
| 210 | 220 | 230 | 240 |
| GAAAGGAGAT | CATATTGCAG | GCATTCGACT | GGGAATCTCA |
| 250 | 260 | 270 | 280 |
| TAAACATGAT | TGGTGGCTAA | ATTTAGATAC | GAAAGTTCCT |
| 290 | 300 | 310 | 320 |
| GATATTGCAA | AGTCTGGTTT | CACAACTGCT | TGGCTGCCTC |
| 330 | 340 | 350 | 360 |
| CGGTGTGTCA | GTCATTGGCT | CCTGAAGGTT | ACCTTCCACA |
| 370 | 380 | 390 | 400 |
| GAACCTTTAT | TCTCTCAATT | CTAAATATGG | TTCTGAGGAT |
| 410 | 420 | 430 | 440 |
| CTCTTAAAAG | CTTTACTTAA | TAAGATGAAG | CAGTACAAAG |
| 450 | 460 | 470 | 480 |
| TTAGAGCGAT | GGCGGACATA | GTCATTAACC | ACCGTGTTGG |
| 490 | 500 | 510 | 520 |
| GACTACTCAA | GGGCATGGTG | GAATGTACAA | CCGCTATGAT |
| 530 | 540 | 550 | 560 |
| GGAATTCCTA | TGTCTTGGGA | TGAACATGCT | ATTACATCTT |
| 570 | 580 | 590 | 600 |
| GCACTGGTGG | AAGGGGTAAC | AAAAGCACTG | GAGACAACTT |
| 610 | 620 | 630 | 640 |
| TAATGGAGTT | CCAAATATAG | ATCATACACA | ATCCTTTGTT |
| 650 | 660 | 670 | 680 |
| CGGAAAGATC | TCATTGACTG | GATGCGGTGG | CTAAGATCCT |
| 690 | 700 | 710 | 720 |
| CTGTTGGCTT | CCAAGATTTT | CGTTTTGATT | TTGCCAAAGG |
| 730 | 740 | 750 | 760 |
| TTATGCTTCA | AAGTATGTAA | AGGAATATAT | CGAGGGAGCT |
| 770 | 780 | 790 | 800 |
| GAGCCAATAT | TTGCAGTTGG | AGAATACTGG | GACACTTGCA |
| 810 | 820 | 830 | 840 |
| ATTACAAGGG | CAGCAATTTG | GATTACAACC | AAGATAGTCA |
| 850 | 860 | 870 | 880 |
| CAGGCAAAGA | ATCATCAATT | GGATTGATGG | CGCGGGACAA |
| 890 | 900 | 910 | 920 |
| CTTTCAACTG | CATTCGATTT | TACAACAAAA | GCAGTCCTTC |

FIG. 4(I)

| 930 | 940 | 950 | 960 |
|---|---|---|---|
| AGGAAGCAGT | CAAAGGAGAA | TTCTGGCGTT | TGCGTGACTC |
| 970 | 980 | 990 | 1000 |
| TAAGGGGAAG | CCCCCAGGAG | TTTTAGGATT | GTGGCCTTCA |
| 1010 | 1020 | 1030 | 1040 |
| AGGGCTGTCA | CTTTTATTGA | TAATCACGAC | ACTGGATCAA |
| 1050 | 1060 | 1070 | 1080 |
| CTCAGGCGCA | TTGGCCTTTC | CCTTCACGTC | ATGTTATGGA |
| 1090 | 1100 | 1110 | 1120 |
| GGGCTATGCA | TACATTCTTA | CACACCCAGG | GATACCATCA |
| 1130 | 1140 | 1150 | 1160 |
| GTTTTCTTTG | ACCATTTCTA | CGAATGGGAT | AATTCCATGC |
| 1170 | 1180 | 1190 | 1200 |
| ATGACCAAAT | TGTAAAGCTG | ATTGCTATTC | GGAGGAATCA |
| 1210 | 1220 | 1230 | 1240 |
| AGGCATACAC | AGCCGTTCAT | CTATAAGAAT | TCTTGAGGCA |
| 1250 | 1260 | 1270 | 1280 |
| CAGCCAAACT | TATACGCTGC | AACCATTGAT | GAAAAGGTTA |
| 1290 | 1300 | 1310 | 1320 |
| GCGTGAAGAT | TGGGGACGGA | TCATGGAGCC | CTGCTGGGAA |
| 1330 | 1340 | 1350 | 1360 |
| AGAGTGGACT | CTCGCGACCA | GTGGCCATCG | CTATGCAGTC |
| 1370 | 1380 | 1390 | 1400 |
| TGGCAGAAGT | AATCTTACAG | CTATTCCGTT | ACTTAATATA |
| 1410 | 1420 | 1430 | 1440 |
| TTAGTAGAAA | TATATATGTT | TTAAACCCGA | GCACCTACTT |
| 1450 | 1460 | 1470 | 1480 |
| CTAACACTAG | ATCCGCCTCT | ACAGGCTTGG | ATGGAGTGAT |
| 1490 | 1500 | 1510 | 1520 |
| GAGTTTTTTT | TTCCTGTTCA | TTAGACATTG | CAACATGGGA |
| 1530 | 1540 | 1550 | 1560 |
| TGTATGTTTT | GTTAATAAAA | GTGTTCTTGA | TCAATGCAAT |
| 1570 | | | |
| GTAATAAGGG | | | |

FIG. 4(II)

SEQUENCE: Nucleotide sequence of a cDNA encoding the large subunit of ADP-glucose pyrophosphorylase from barley seed endosperm (bepl10) .
SEQUENCE TYPE: NUCLEIC ACID
MOLECULE TYPE: DNA
ORIGINAL SOURCE: BARLEY
SEQUENCE LENGTH: 2037
STRANDEDNESS: DOUBLE
TOPOLOGY: LINEAR

```
1     ACGACCACCT CCGAACTCAA CGCCTCCACG GACCATCTCT
41    CTCCTCTCCC CTCCCCTCAC CACCACCACC ACCACCACCC
81    CTTCTCCCTC CCTGCATTTG ATTCGTTCAT ATTCATCCGT
121   CGCTTGCCCG GTCGCCACCC CGTCGATCCC TCACCCCGCC
161   GTCCCCGGCA GTTGCAGGTG GACTGCTAAT GTCATCGATG
201   CAGTTCAGCA GCGTGCTGCC CCTGGAGGGC AAGGCGTGCG
241   TTTCCCCAGT CAGGAGAGAG GGATCGGCCT GCGAGCGCCT
281   CAAGATCGGG GACAGCAGCA GCATCAGGCA CGAGAGAGCG
321   TCCAGGAGGA TGTGCAACGG CGGCGCAGGG GCCCCGCCGC
361   CACCGGTGCG CAGTGCGTGC TCACCTCCGA CGCCAGCCCG
401   GCCGACACCC TTGTTCTCCG GACGTCCTTC CGGAGGAATT
      ACGCCGATCC GAACGAGGTC GCGGCCGTCG GTCGCGGCCG
      TCATACTCGG CGGCGGCACC GGGACTCAGC TCTTCCCGCT
      CACAAGCACA AGGGCCACAC CTGCTGTTCC TATTGGAGGA
      TGTTACAGGC TCATCGATAT TCCCATGAGC AACTGCTTCA
601   ACAGTGGCAT CAACAAGATA TTCGTCATGA CCCAGTTCAA
      CTCGGCATCT CTCAATCGCC ACATTCACCG CACCTACCTC
      GGCGGGGGAA TCAATTTCAC TGATGGATCT GTTGAGGTAT
      TGGCCGCGAC ACAAATGCCT GGGGAGGCTG CTGGATGGTT
      CCGCGGAACA GCGGATGCCG TCAGAAAATT TATCTGGGTG
801   CTTGAGGACT ACTATAAGCA TAAATCCATA GAGCACATTT
      TGATCTTGTC GGGCGATCAG CTTTATCGCA TGGATTACAT
      GGAGCTTGTG CAGAAACATG TGGATGACAA TGCTGACATT
      ACTTTATCAT GTGCCCCTGT TGGAGAGAGC CGGGCATCTG
      AGTACGGGCT AGTGAAGTTC GACAGTTCAG GCCGTGTGAT
1001  CCAGTTTTCT GAGAAGCCAA AGGGCGACGA TCTGGAAGCG
      ATGAAAGTGG ATACCAGTTT TCTCAATTTC GCCATAGACG
      ACCCTGCTAA ATATCCATAC ATTGCTTCGA TGGGAGTTTA
      TGTCTTCAAG AGAGATGTTC TGCTGAACCT TCTAAAGTCA
      AGATACGCAG AACTACATGA CTTTGGGTCT GAAATCCTCC
1201  CGAGAGCTCT GCATGATCAC AATGTACAGG CATATGTCTT
      CACTGACTAC TGGGAGGACA TTGGAACAAT CAGATCCTTC
      TTCGATGCGA ACATGGCCCT CTGCGAACAG CCTCCAAAGT
      TTGAATTTTA TGATCCAAAA ACCCCCTTCT TCACTTCGCC
      TCGGTACTTA CCGCCAACAA AGTCAGACAA GTGCAGGATC
1401  AAAGAAGCGA TCATTTCGCA CGGCTGCTTC TTGCGTGAAT
      GCAAAATCGA GCACTCCATC ATCGGCGTTC GTTCACGCCT
      AAACTCCGGA AGCGAGCTCA AGAACGCGAT GATGATGGGC
      GCGGACTCGT ACGAGACCGA GGACGAGATC TCGAGGCTGA
      TGTCTGAGGG CAAGGTTCCC ATCGGCGTCG GGGAGAACAC
1601  AAAGATCAGC AACTGCATCA TCGACATGAA CGCGAGGATA
```

FIG. 5(I)

```
      GGAAGGGACG TGGTCATCTC AAACAAGGAG GGGGTGCAAG
      AAGCCGACAG GCCGGAGGAA GGGTACTACA TCAGGTCCGG
      GATCGTGGTG ATCCAGAAGA ACGCGACCAT CAAGGACGGC
      ACCGTCGTGT AGGGCGTGCC GGGTCGGCGC GACGGGGTTC
1801  TGCGACAACC TGTGCGCTGC GTCGGTCGTC ATCATCTTCT
      CAAACTCCGG GACTGAAGAA GTGATCCGGG GACGGGAGAC
      GTTTGAAGCT TGAATGACTG AGACTGAAAG TGAAGGCGCA
      GCAGAGGCAG GCAGCATTAG TAGTAAGTAG TAAGTAAGTA
      GCAGTGGAAC AAAGTAATAG TCGTTCGTTT TTCCCCTGTA
2001  ATAAATAAGA GGCTGTGTGT TGAGGTAAAA AAAAAAA
```

FIG. 5(II)

SEQUENCE: Nucleotide sequence of a cDNA encoding the small subunit of ADP-glucose pyrophosphorylase from barley seed endosperm (beps)
SEQUENCE TYPE: NUCLEIC ACID
MOLECULE TYPE: DNA
ORIGINAL SOURCE: BARLEY
SEQUENCE LENGTH: 1822
STRANDEDNESS: DOUBLE
TOPOLOGY: LINEAR
COMMENT: The "." at 1569 denotes a purine.

```
1     AAAAGTGAAC TCACACATCA CTCAATATCT ATATCCTTCC
      ATTTTATATC CCTCGGTGAT GGATGTACCT TTGGCATCTA
      AAGTTCCCTT GCCCTCCCCT TCCAAGCATG AACAATGCAA
      CGTTTATAGT CATAAGAGCT CATCGAAGCA TGCAGATCTC
      AATCCCCATG CTATTGATAG TGTTCTCGGT ATCATTCTTG
201   GAGGTGGTGC AGGGACTAGA TTGTATCCCC TGACGAAGAA
      GCGTGCAAAG CCTGCAGTGC CATTGGGTGC CAACTACAGG
      CTTATTGATA TTCCTGTCAG TAATTGTCTG AACAGCAACA
      TATCAAAGAT CTATGTGCTT ACACAGTTCA ACTCAGCTTC
      TCTTAATCGT CATCTCTCAC GAGCCTATGG GAGCAACATT
401   GGAGGTTACA AGAATGAAGG ATTTGTTGAA GTCCTTGCTG
      CACAGCAGAG CCCAGATAAC CCTGACTGGT TCCAGGGTAC
      TGCAGATGCT GTAAGGCAGT ACTTGTGGCT ATTCGAGGAG
      CATAATGTTA TGGAGTATCT AATTCTTGCT GGAGATCACC
      TGTACCGAAT GGACTATGAA AAGTTTATTC AGGCACACAG
601   AGAAACGGAT GCTGATATTA CTGTTGCTGC CTTGCCCATG
      GATGAGGAAC GTGCAACTGC ATTTGGCCTT ATGAAAATCG
      ATGAAGAAGG GAGGATAATT GAATTCGCAG AGAAACCAAA
      AGGAGAACAG TTGAAAGCTA TGATGGTTGA TACGACCATA
      CTTGGCCTTG AAGATGCGAG GGCAAAGGAA ATGCCTTATA
801   TTGCTAGCAT GGGTATCTAT GTTATTAGCA AACATGTGAT
      GCTTCAGCTT CTCCGTGAGC AATTTCCTGG AGCTAATGAC
      TTCGGAAGTG AAGTTATCCC TGGTGCAACT AGCACTGGCA
      TGAGGGTACA AGCATACCTA TACGACGGTT ACTGGGAAGA
      TATTGGTACA ATTGAGGCAT TCTATAATGC AAATTTGGGA
1001  ATTACCAAAA AACCAATACC TGATTTCAGT TTCTATGACC
      GTTCTGCTCC CATTTACACA CAACCTCGAC ACTTGCCTCC
      TTCAAAGGTT CTTGATGCTG ATGTGACAGA CAGTGTAATT
      GGTGAAGGAT GTGTTATTAA AAACTGCAAG ATACACCATT
      CAGTAGTTGG ACTCCGTTCC TGCATATCTG AAGGTGCAAT
1201  AATAGAGGAC ACGTTGCTAA TGGGTGCGGA CTACTATGAG
      ACTGAAGCTG ATAAGAAACT CCTTGCTGAA AAAGGTGGCA
      TTCCCATTGG TATTGGAAAG AATTCACACA TCAAAAGAGC
      AATCATTGAC AAGAATGCTC GTATTGGAGA TAACGTGATG
      ATAATCAATG TTGACAATGT TCAAGAAGCG GCGAGGGAGA
1401  CAGATGGATA CTTCATCAAA AGTGGCATCG TAACTGTGAT
      CAAGGATGCT TTACTCCCTA GTGGAACAGT CATATGAAGC
      AGATGTGAAA TGTATGCCAA AAGACAGGGC TACTTGCGTC
      AGTCTGGAAT CAACCAACAA GGCCGCGAAG GAGATCATAA
      AATAAAAA.G GAGTGCCATG CGAGTCACTT CTACACCCTT
1601  TTCCCCCCTT GATGTATTAG GAACTGTGAT GTACAAGCAA
```

FIG. 6(I)

```
      CTGTGATGCA CTTACGCGAA GTGCCCCTGG ATTCAGCTTT
      CTCTTTGCTT GTAACTGGTT TCCAGCAGAC CATGCTATTT
      GTTGTATGGT TCGTGCAAAA CCTTGCGATG CTTTATATAT
      GCTTTATATA TAAACAAGAT GAATCCCCGC GCGTTGCTGC
2001  GGCACAAAAA AAAAAAAAAA AA
```

FIG. 6(II)

α-GLUCAN LYASE CODING SEQUENCE
SEQUENCE TYPE: NUCLEIC ACID
MOLECULE TYPE: DNA (GENOMIC)
ORIGINAL SOURCE: FUNGALLY INFECTED ALGAE
SEQUENCE LENGTH: 3267 BP
STRANDEDNESS: DOUBLE
SEQUENCE:

```
                10         20         30         40         50         60
                 |          |          |          |          |          |
   1 ATGTTTTCAA CCCTTGCGTT TGTCGCACCT AGTGCGCTGG GAGCCAGTAC CTTCGTAGGG
  61 GCGGAGGTCA GGTCAAATGT TCGTATCCAT TCCGCTTTTC CAGCTGTGCA CACAGCTACT
 121 CGCAAAACCA ATCGCCTCAA TGTATCCATG ACCGCATTGT CCGACAAACA AACGGCTACT
 181 GCGGGTAGTA CAGACAATCC GGACGGTATC GACTACAAGA CCTACGATTA CGTCGGAGTA
 241 TGGGGTTTCA GCCCCCTCTC CAACACGAAC TGGTTTGCTG CCGGCTCTTC TACCCCGGGT
 301 GGCATCACTG ATTGGACGGC TACAATGAAT GTCAACTTCG ACCGTATCGA CAATCCGTCC
 361 ATCACTGTCC AGCATCCCGT TCAGGTTCAG GTCACGTCAT ACAACAACAA CAGCTACAGG
 421 GTTCGCTTCA ACCCTGATGG CCCTATTCGT GATGTGACTC GTGGGCCTAT CCTCAAGCAG
 481 CAACTAGATT GGATTCGAAC GCAGGAGCTG TCAGAGGGAT GTGATCCCGG AATGACTTTC
 541 ACATCAGAAG GTTTCTTGAC TTTTGAGACC AAGGATCTAA GCGTCATCAT CTACGGAAAT
 601 TTCAAGACCA GAGTTACGAG AAAGTCTGAC GGCAAGGTCA TCATGGAAAA TGATGAAGTT
 661 GGAACTGCAT CGTCCGGGAA CAAGTGCCGG GGATTGATGT TCGTTGATAG ATTATACGGT
 721 AACGCTATCG CTTCCGTCAA CAAGAACTTC CGCAACGACG CGGTCAAGCA GGAGGGATTC
 781 TATGGTGCAG GTGAAGTCAA CTGTAAGTAC CAGGACACCT ACATCTTAGA ACGCACTGGA
 841 ATCGCCATGA CAAATTACAA CTACGATAAC TTGAACTATA ACCAGTGGGA CCTTAGACCT
 901 CCGCATCATG ATGGTGCCCT CAACCCAGAC TATTATATTC CAATGTACTA CGCAGCACCT
 961 TGGTTGATCG TTAATGGATG CGCCGGTACT TCGGAGCAGT ACTCGTATGG ATGGTTCATG
1021 GACAATGTCT CTCAATCTTA CATGAATACT GGAGATACTA CCTGGAATTC TGGACAAGAG
1081 GACCTGGCAT ACATGGGCGC GCAGTATGGA CCATTTGACC AACATTTTGT TTACGGTGCT
1141 GGGGGTGGGA TGGAATGTGT GGTCACAGCG TTCTCTCTTC TACAAGGCAA GGAGTTCGAG
1201 AACCAAGTTC TCAACAAACG TTCAGTAATG CCTCCGAAAT ACGTCTTTGG TTTCTTCCAG
1261 GGTGTTTTCG GGACTTCTTC CTTGTTGAGA GCGCATATGC CAGCAGGTGA GAACAACATC
1321 TCAGTCGAAG AAATTGTAGA AGGTTATCAA AACAACAATT TCCCTTTCGA GGGGCTCGCT
1381 GTGGACGTGG ATATGCAAGA CAACTTGCGG GTGTTCACCA CGAAGGGCGA ATTTTGGACC
1441 GCAAACAGGG TGGGTACTGG CGGGGATCCA AACAACCGAT CGGTTTTTGA ATGGGCACAT
1501 GACAAAGGCC TTGTTTGTCA GACAAATATA ACTTGCTTCC TGAGGAATGA TAACGAGGGG
1561 CAAGACTACG AGGTCAATCA GACGTTAAGG GAGAGGCAGT TGTACACGAA GAACGACTCC
1621 CTGACGGGTA CGGATTTTGG AATGACCGAC GACGGCCCCA GCGATGCGTA CATCGGTCAT
1681 CTGGACTATG GGGGTGGAGT AGAATGTGAT GCACTTTTCC CAGACTGGGG ACGGCCTGAC
1741 GTGGCCGAAT GGTGGGGAAA TAACTATAAG AAACTGTTCA GCATTGGTCT CGACTTCGTC
1801 TGGCAAGACA TGACTGTTCC AGCAATGATG CCGCACAAAA TTGGCGATGA CATCAATGTG
1861 AAACCGGATG GGAATTGGCC GAATGCGGAC GATCCGTCCA ATGGACAATA CAACTGGAAG
1921 ACGTACCATC CCCAAGTGCT TGTAACTGAT ATGCGTTATG AGAATCATGG TCGGGAACCG
1981 ATGGTCACTC AACGCAACAT TCATGCGTAT ACACTGTGCG AGTCTACTAG GAAGGAAGGG
2041 ATCGTGGAAA ACGCAGACAC TCTAACGAAG TTCCGCCGTA GCTACATTAT CAGTCGTGGT
2101 GGTTACATTG GTAACCAGCA TTTCGGGGGT ATGTGGGTGG GAGACAACTC TACTACATCA
2161 AACTACATCC AAATGATGAT TGCCAACAAT ATTAACATGA ATATGTCTTG CTTGCCTCTC
2221 GTCGGCTCCG ACATTGGAGG ATTCACCTCA TACGACAATG AGAATCAGCG AACGCCGTGT
2281 ACCGGGGACT TGATGGTGAG GTATGTGCAG GCGGGCTGCC TGTTGCCGTG GTTCAGGAAC
2341 CACTATGATA GGTGGATCGA GTCCAAGGAC CACGGAAAGG ACTACCAGGA GCTGTACATG
2401 TATCCGAATG AAATGGATAC GTTGAGGAAG TTCGTTGAAT TCCGTTATCG CTGGCAGGAA
2461 GTGTTGTACA CGGCCATGTA CCAGAATGCG GCTTTCGGAA AGCCGATTAT CAAGGCTGCT
2521 TCGATGTACA ATAACGACTC AAACGTTCGC AGGGCGCAGA ACGATCATTT CCTTCTTGGT
2581 GGACATGATG GATATCGCAT TCTGTGCGCG CCTGTTGTGT GGGAGAATTC GACCGAACGC
```

FIG. 7(I)

```
2641 GAATTGTACT TGCCCGTGCT GACCCAATGG TACAAATTCG GTCCCGACTT TGACACCAAG
2701 CCTCTGGAAG GAGCGATGAA CGGAGGGGAC CGAATTTACA ACTACCCTGT ACCGCAAAGT
2761 GAATCACCAA TCTTCGTGAG AGAAGGTGCG ATTCTCCCTA CCCGCTACAC GTTGAACGGT
2821 GAAAACAAAT CATTGAACAC GTACACGGAC GAAGATCCGT TGGTGTTTGA AGTATTCCCC
2881 CTCGGAAACA ACCGTGCCGA CGGTATGTGT TATCTTGATG ATGGCGGTGT GACCACCAAT
2941 GCTGAAGACA ATGGCAAGTT CTCTGTCGTC AAGGTGGCAG CGGAGCAGGA TGGTGGTACG
3001 GAGACGATAA CGTTTACGAA TGATTGCTAT GAGTACGTTT TCGGTGGACC GTTCTACGTT
3061 CGAGTGCGCG GCGCTCAGTC GCCGTCGAAC ATCCACGTGT CTTCTGGAGC GGGTTCTCAG
3121 GACATGAAGG TGAGCTCTGC CACTTCCAGG GCTGCGCTGT TCAATGACGG GGAGAACGGT
3181 GATTTCTGGG TTGACCAGGA GACAGATTCT CTGTGGCTGA AGTTGCCCAA CGTTGTTCTC
3241 CCGGACGCTG TGATCACAAT TACCTAA
```

FIG. 7(II)

α-GLUCAN LYASE CODING SEQUENCE
SEQUENCE TYPE: NUCLEIC ACID
MOLECULE TYPE: DNA (GENOMIC)
ORIGINAL SOURCE: FUNGALLY INFECTED ALGAE
SEQUENCE LENGTH: 3276 BP
STRANDEDNESS: DOUBLE
SEQUENCE:

```
              10         20         30         40         50         60
               |          |          |          |          |          |
   1 ATGTATCCAA CCCTCACCTT CGTGGCGCCT AGTGCGCTAG GGGCCAGAAC TTTCACGTGT
  61 GTGGGCATTT TTAGGTCACA CATTCTTATT CATTCGGTTG TTCCAGCGGT GCGTCTAGCT
 121 GTGCGCAAAA GCAACCGCCT CAATGTATCC ATGTCCGCTT TGTTCGACAA ACCGACTGCT
 181 GTTACTGGAG GGAAGGACAA CCCGGACAAT ATCAATTACA CCACTTATGA CTACGTCCCT
 241 GTGTGGCGCT TCGACCCCCT CAGCAATACG AACTGGTTTG CTGCCGGATC TTCCACTCCC
 301 GGCGATATTG ACGACTGGAC GGCGACAATG AATGTGAACT TCGACCGTAT CGACAATCCA
 361 TCCTTCACTC TCGAGAAACC GGTTCAGGTT CAGGTCACGT CATACAAGAA CAATTGTTTC
 421 AGGGTTCGCT TCAACCCTGA TGGTCCTATT CGCGATGTGG ATCGTGGGCC TATCCTCCAG
 481 CAGCAACTAA ATTGGATCCG GAAGCAGGAG CAGTCGAAGG GGTTTGATCC TAAGATGGGC
 541 TTCACAAAAG AAGGTTTCTT GAAATTTGAG ACCAAGGATC TGAACGTTAT CATATATGGC
 601 AATTTTAAGA CTAGAGTTAC GAGGAAGAGG GATGGAAAAG GGATCATGGA GAATAATGAA
 661 GTGCCGGCAG GATCGTTAGG GAACAAGTGC CGGGGATTGA TGTTTGTCGA CAGGTTGTAC
 721 GGCACTGCCA TCGCTTCCGT TAATGAAAAT TACCGCAACG ATCCCGACAG GAAAGAGGGG
 781 TTCTATGGTG CAGGAGAAGT AAACTGCGAG TTTTGGGACT CCGAACAAAA CAGGAACAAG
 841 TACATCTTAG AACGAACTGG AATCGCCATG ACAAATTACA ATTATGACAA CTATAACTAC
 901 AACCAGTCAG ATCTTATTGC TCCAGGATAT CCTTCCGACC CGAACTTCTA CATTCCCATG
 961 TATTTTGCAG CACCTTGGGT AGTTGTTAAG GGATGCAGTG GCAACAGCGA TGAACAGTAC
1021 TCGTACGGAT GGTTTATGGA TAATGTCTCC CAAACTTACA TGAATACTGG TGGTACTTCC
1081 TGGAACTGTG GAGAGGAGAA CTTGGCATAC ATGGGAGCAC AGTGCGGTCC ATTTGACCAA
1141 CATTTTGTGT ATGGTGATGG AGATGGTCTT GAGGATGTTG TCCAAGCGTT CTCTCTTCTG
1201 CAAGGCAAAG AGTTTGAGAA CCAAGTTCTG AACAAACGTG CCGTAATGCC TCCGAAATAT
1261 GTGTTTGGTT ACTTTCAGGG AGTCTTTGGG ATTGCTTCCT TGTTGAGAGA GCAAAGACCA
1321 GAGGGTGGTA ATAACATCTC TGTTCAAGAG ATTGTCGAAG GTTACCAAAG CAATAACTTC
1381 CCTTTAGAGG GGTTAGCCGT AGATGTGGAT ATGCAACAAG ATTTGCGCGT GTTCACCACG
1441 AAGATTGAAT TTTGGACGGC AAATAAGGTA GGCACCGGGG GAGACTCGAA TAACAAGTCG
1501 GTGTTTGAAT GGGCACATGA CAAAGGCCTT GTATGTCAGA CGAATGTTAC TTGCTTCTTG
1561 AGAAACGACA ACGGCGGGGC AGATTACGAA GTCAATCAGA CATTGAGGGA GAAGGGTTTG
1621 TACACGAAGA ATGACTCACT GACGAACACT AACTTCGGAA CTACCAACGA CGGGCCGAGC
1681 GATGCGTACA TTGGACATCT GGACTATGGT GGCGGAGGGA ATTGTGATGC ACTTTTCCCA
1741 GACTGGGGTC GACCGGGTGT GGCTGAATGG TGGGGTGATA ACTACAGCAA GCTCTTCAAA
1801 ATTGGTCTGG ATTTCGTCTG GCAAGACATG ACAGTTCCAG CTATGATGCC ACACAAAGTT
1861 GGCGACGCAG TCGATACGAG ATCACCTTAC GGCTGGCCGA ATGAGAATGA TCCTTCGAAC
1921 GGACGATACA ATTGGAAATC TTACCATCCA CAAGTTCTCG TAACTGATAT GCGATATGAG
1981 AATCATGGAA GGGAACCGAT GTTCACTCAA CGCAATATGC ATGCGTACAC ACTCTGTGAA
2041 TCTACGAGGA AGGAAGGGAT TGTTGCAAAT GCAGACACTC TAACGAAGTT CCGCCGCAGT
2101 TATATTATCA GTCGTGGAGG TTACATTGGC AACCAGCATT TTGGAGGAAT GTGGGTTGGA
2161 GACAACTCTT CCTCCCAAAG ATACCTCCAA ATGATGATCG CGAACATCGT CAACATGAAC
2221 ATGTCTTGCC TTCCACTAGT TGGGTCCGAC ATTGGAGGTT TTACTTCGTA TGATGGACGA
2281 AACGTGTGTC CCGGGGATCT AATGGTAAGA TTCGTGCAGG CGGGTTGCTT ACTACCGTGG
2341 TTCAGAAACC ACTATGGTAG GTTGGTCGAG GGCAAGCAAG AGGGAAAATA CTATCAAGAA
2401 CTGTACATGT ACAAGGACGA GATGGCTACA TTGAGAAAAT TCATTGAATT CCGTTACCGC
2461 TGGCAGGAGG TGTTGTACAC TGCTATGTAC CAGAATGCGG CTTTCGGGAA ACCGATTATC
2521 AAGGCAGCTT CCATGTACGA CAACGACAGA AACGTTCGCG GCGCACAGGA TGACCACTTC
2581 CTTCTCGGCG GACACGATGG ATATCGTATT TTGTGTGCAC CTGTTGTGTG GGAGAATACA
```

FIG. 8(I)

```
2641 ACCAGTCGCG ATCTGTACTT GCCTGTGCTG ACCAAATGGT ACAAATTCGG CCCTGACTAT
2701 GACACCAAGC GCCTGGATTC TGCGTTGGAT GGAGGGCAGA TGATTAAGAA CTATTCTGTG
2761 CCACAAAGCG ACTCTCCGAT ATTTGTGAGG GAAGGAGCTA TTCTCCCTAC CCGCTACACG
2821 TTGGACGGTT CGAACAAGTC AATGAACACG TACACAGACA AAGACCCGTT GGTGTTTGAG
2881 GTATTCCCTC TTGGAAACAA CCGTGCCGAC GGTATGTGTT ATCTTGATGA TGGCGGTATT
2941 ACTACAGATG CTGAGGACCA TGGCAAATTC TCTGTTATCA ATGTCGAAGC CTTACGGAAA
3001 GGTGTTACGA CGACGATCAA GTTTGCGTAT GACACTTATC AATACGTATT TGATGGTCCA
3061 TTCTACGTTC GAATCCGTAA TCTTACGACT GCATCAAAAA TTAACGTGTC TTCTGGAGCG
3121 GGTGAAGAGG ACATGACACC GACCTCTGCG AACTCGAGGG CAGCTTTGTT CAGTGATGGA
3181 GGTGTTGGAG AATACTGGGC TGACAATGAT ACGTCTTCTC TGTGGATGAA GTTGCCAAAC
3241 CTGGTTCTGC AAGACGCTGT GATTACCATT ACGTAG
```

FIG. 8(II)

α-GLUCAN LYASE CODING SEQUENCE
SEQUENCE TYPE: NUCLEIC ACID
MOLECULE TYPE: DNA (GENOMIC)
ORIGINAL SOURCE: FUNGUS
SEQUENCE LENGTH: 3201 BP
STRANDEDNESS: DOUBLE
SEQUENCE:

```
        10         20         30         40         50         60
ATGGCAGGAT TTTCTGATCC TCTCAACTTT TGCAAAGCAG AAGACTACTA CAGTGTTGCG
        70         80         90        100        110        120
CTAGACTGGA AGGGCCCTCA AAAAATCATT GGAGTAGACA CTACTCCTCC AAAGAGCACC
       130        140        150        160        170        180
AAGTTCCCCA AAAACTGGCA TGGAGTGAAC TTGAGATTCG ATGATGGGAC TTTAGGTGTG
       190        200        210        220        230        240
GTTCAGTTCA TTAGGCCGTG CGTTTGGAGG GTTAGATACG ACCCTGGTTT CAAGACCTCT
       250        260        270        280        290        300
GACGAGTATG GTGATGAGAA TACGAGGACA ATTGTGCAAG ATTATATGAG TACTCTGAGT
       310        320        330        340        350        360
AATAAATTGG ATACTTATAG AGGTCTTACG TGGGAAACCA AGTGTGAGGA TTCGGGAGAT
       370        380        390        400        410        420
TTCTTTACCT TCTCATCCAA GGTCACCGCC GTTGAAAAAT CCGAGCGGAC CCGCAACAAG
       430        440        450        460        470        480
GTCGGCGATG GCCTCAGAAT TCACCTATGG AAAAGCCCTT TCCGCATCCA AGTAGTGCGC
       490        500        510        520        530        540
ACCTTGACCC CTTTGAAGGA TCCTTACCCC ATTCCAAATG TAGCCGCAGC CGAAGCCCGT
       550        560        570        580        590        600
GTGTCCGACA AGGTCGTTTG GCAAACGTCT CCCAAGACAT TCAGAAAGAA CCTGCATCCG
       610        620        630        640        650        660
CAACACAAGA TGCTAAAGGA TACAGTTCTT GACATTGTCA AACCTGGACA TGGCGAGTAT
       670        680        690        700        710        720
GTGGGGTGGG GAGAGATGGG AGGTATCCAG TTTATGAAGG AGCCAACATT CATGAACTAT
       730        740        750        760        770        780
TTTAACTTCG ACAATATGCA ATACCAGCAA GTCTATGCCC AAGGTGCTCT CGATTCTCGC
       790        800        810        820        830        840
GAGCCACTGT ACCACTCGGA TCCCTTCTAT CTTGATGTGA ACTCCAACCC GGAGCACAAG
       850        860        870        880        890        900
AATATCACGG CAACCTTTAT CGATAACTAC TCTCAAATTG CCATCGACTT TGGAAAGACC
       910        920        930        940        950        960
AACTCAGGCT ACATCAAGCT GGGAACCAGG TATGGTGGTA TCGATTGTTA CGGTATCAGT
       970        980        990       1000       1010       1020
GCGGATACGG TCCCGGAAAT TGTACGACTT TATACAGGTC TTGTTGGACG TTCAAAGTTG
      1030       1040       1050       1060       1070       1080
AAGCCCAGAT ATATTCTCGG GGCCCATCAA GCCTGTTATG GATACCAACA GGAAAGTGAC
      1090       1100       1110       1120       1130       1140
TTGTATTCTG TGGTCCAGCA GTACCGTGAC TGTAAATTTC CACTTGACGG GATTCACGTC
      1150       1160       1170       1180       1190       1200
GATGTCGATG TTCAGGACGG CTTCAGAACT TTCACCACCA ACCCACACAC TTTCCCTAAC
      1210       1220       1230       1240       1250       1260
CCCAAAGAGA TGTTTACTAA CTTGAGGAAT AATGGAATCA AGTGCTCCAC CAATATCACT
      1270       1280       1290       1300       1310       1320
CCTGTTATCA GCATTAACAA CAGAGAGGGT GGATACAGTA CCCTCCTTGA GGGAGTTGAC
```

FIG. 9(I)

```
      1330       1340       1350       1360       1370       1380
AAAAAATACT TTATCATGGA CGACAGATAT ACCGAGGGAA CAAGTGGGAA TGCGAAGGAT
      1390       1400       1410       1420       1430       1440
GTTCGGTACA TGTACTACGG TGGTGGTAAT AAGGTTGAGG TCGATCCTAA TGATGTTAAT
      1450       1460       1470       1480       1490       1500
GGTCGGCCAG ACTTTAAAGA CAACTATGAC TTCCCCGCGA ACTTCAACAG CAAACAATAC
      1510       1520       1530       1540       1550       1560
CCCTATCATG GTGGTGTGAG CTACGGTTAT GGGAACGGTA GTGCAGGTTT TTACCCGGAC
      1570       1580       1590       1600       1610       1620
CTCAACAGAA AGGAGGTTCG TATCTGGTGG GGAATGCAGT ACAAGTATCT CTTCGATATG
      1630       1640       1650       1660       1670       1680
GGACTGGAAT TTGTGTGGCA AGACATGACT ACCCCAGCAA TCCACACATC ATATGGAGAC
      1690       1700       1710       1720       1730       1740
ATGAAAGGGT TGCCCACCCG TCTACTCGTC ACCTCAgACT CCGTCACCAA TGCCTCTGAG
      1750       1760       1770       1780       1790       1800
AAAAAGCTCG CAATTGAAAC TTGGGCTCTC TACTCCTACA ATCTCCACAA AGCAACTTGG
      1810       1820       1830       1840       1850       1860
CATGGTCTTA GTCGTCTCGA ATCTCGTAAG AACAAACGAA ACTTCATCCT CGGGCGTGGA
      1870       1880       1890       1900       1910       1920
AGTTATGCCG GAGCCTATCG TTTTGCTGGT CTCTGGACTG GGGATAATGC AAGTAACTGG
      1930       1940       1950       1960       1970       1980
GAATTCTGGA AGATATCGGT CTCTCAAGTT CTTTCTCTGG GCCTCAATGG TGTGTGCATC
      1990       2000       2010       2020       2030       2040
GCGGGGTCTG ATACGGGTGG TTTTGAACCC TACCGTGATG CAAATGGGGT CGAGGAGAAA
      2050       2060       2070       2080       2090       2100
TACTGTAGCC CAGAGCTACT CATCAGGTGG TATACTGGTT CATTCCTCTT GCCGTGGCTC
      2110       2120       2130       2140       2150       2160
AGGAACCATT ATGTCAAAAA GGACAGGAAA TGGTTCCAGG AACCATACTC GTACCCCAAG
      2170       2180       2190       2200       2210       2220
CATCTTGAAA CCCATCCAGA ACTCGCAGAC CAAGCATGGC TCTATAAATC CGTTTTGGAG
      2230       2240       2250       2260       2270       2280
ATCTGTAGGT ACTATGTGGA GCTTAGATAC TCCCTCATCC AACTACTTTA CGACTGCATG
      2290       2300       2310       2320       2330       2340
TTTCAAAACG TaGTCGACGG TATGCCAATC ACCAGATCTA TGCTCTTGAC CGATACTGAG
      2350       2360       2370       2380       2390       2400
GATACCACCT TCTTCAACGA GAGCCAAAAG TTCCTCGACA ACCAATATAT GGCTGGTGAC
      2410       2420       2430       2440       2450       2460
GACATTCTTG TTGCACCCAT CCTCCACAGT CGCAAAGAAA TTCCAGGCGA AAACAGAGAT
      2470       2480       2490       2500       2510       2520
GTCTATCTCC CTCTTTACCA CACCTGGTAC CCCTCAAATT TGAGACCATG GGACGATCAA
      2530       2540       2550       2560       2570       2580
GGAGTCGCTT TGGGGAATCC TGTCGAAGGT GGTAGTGTCA TCAATTATAC TGCTAGGATT
      2590       2600       2610       2620       2630       2640
GTTGCACCCG AGGATTATAA TCTCTTCCAC AGCGTGGTAC CAGTCTACGT TAGAGAGGGT
      2650       2660       2670       2680       2690       2700
GCCATCATCC CGCAAATCGA AGTACGCCAA TGGACTGGCC AGGGGGGAGC CAACCGCATC
      2710       2720       2730       2740       2750       2760
AAGTTCAACA TCTACCCTGG AAAGGATAAG GAGTACTGTA CCTATCTTGA TGATGGTGTT
      2770       2780       2790       2800       2810       2820
AGCCGTGATA GTGCGCCGGA AGACCTCCCA CAGTACAAAG AGACCCACGA ACAGTCGAAG
      2830       2840       2850       2860       2870       2880
GTTGAAGGCG CGGAAATCGC AAAGCAGATT GGAAAGAAGA CGGGTTACAA CATCTCAGGA
      2890       2900       2910       2920       2930       2940
```

FIG. 9(II)

```
ACCGACCCAG AAGCAAAGGG TTATCACCGC AAAGTTGCTG TCACACAAAC GTCAAAAGAC
      2950       2960       2970       2980       2990       3000
AAGACGCGTA CTGTCACTAT TGAGCCAAAA CACAATGGAT ACGACCCTTC CAAAGAGGTG
      3010       3020       3030       3040       3050       3060
GGTGATTATT ATACCATCAT TCTTTGGTAC GCACCAGGTT TCGATGGCAG CATCGTCGAT
      3070       3080       3090       3100       3110       3120
GTGAGCAAGA CGACTGTGAA TGTTGAGGGT GGGGTGGAGC ACCAAGTTTA TAAGAACTCC
      3130       3140       3150       3160       3170       3180
GATTTACATA CGGTTGTTAT CGACGTGAAG GAGGTGATCG GTACCACAAA GAGCGTCAAG
      3190       3200
ATCACATGTA CTGCCGCTTA A
```

FIG. 9(III)

α-GLUCAN LYASE CODING SEQUENCE
SEQUENCE TYPE: NUCLEIC ACID
MOLECULE TYPE: DNA (GENOMIC)
ORIGINAL SOURCE: FUNGUS
SEQUENCE LENGTH: 3213 BP
STRANDEDNESS: DOUBLE
SEQUENCE:

10 20 30 40 50 60
ATGGCAGGAT TATCCGACCC TCTCAATTTC TGCAAAGCAG AGGACTACTA CGCTGCTGCC
70 80 90 100 110 120
AAAGGCTGGA GTGGCCCTCA GAAGATCATT CGCTATGACC AGACCCCTCC TCAGGGTACA
130 140 150 160 170 180
AAAGATCCGA AAAGCTGGCA TGCGGTAAAC CTTCCTTTCG ATGACGGGAC TATGTGTGTA
190 200 210 220 230 240
GTGCAATTCG TCAGACCCTG TGTTTGGAGG GTTAGATATG ACCCCAGTGT CAAGACTTCT
250 260 270 280 290 300
GATGAGTACG GCGATGAGAA TACGAGGACT ATTGTACAAG ACTACATGAC TACTCTGGTT
310 320 330 340 350 360
GGAAACTTGG ACATTTTCAG AGGTCTTACG TGGGTTTCTA CGTTGGAGGA TTCGGGCGAG
370 380 390 400 410 420
TACTACACCT TCAAGTCCGA AGTCACTGCC GTGGACGAAA CCGAACGGAC TCGAAACAAG
430 440 450 460 470 480
GTCGGCGACG GCCTCAAGAT TTACCTATGG AAAAATCCCT TTCGCATCCA GGTAGTGCGT
490 500 510 520 530 540
CTCTTGACCC CCCTGGTGGA CCCTTTCCCC ATTCCCAACG TAGCCAATGC CACAGCCCGT
550 560 570 580 590 600
GTGGCCGACA AGGTTGTTTG GCAGACGTCC CCGAAGACGT TCAGGAAAAA CTTGCATCCG
610 620 630 640 650 660
CAGCATAAGA TGTTGAAGGA TACAGTTCTT GATATTATCA AGCCGGGGCA CGGAGAGTAT
670 680 690 700 710 720
GTGGGTTGGG GAGAGATGGG AGGCATCGAG TTTATGAAGG AGCCAACATT CATGAATTAT
730 740 750 760 770 780
TTCAACTTTG ACAATATGCA ATATCAGCAG GTCTATGCAC AAGGCGCTCT TGATAGTCGT
790 800 810 820 830 840
GAGCCGTTGT ATCACTCTGA TCCCTTCTAT CTCGACGTGA ACTCCAACCC AGAGCACAAG
850 860 870 880 890 900
AACATTACGG CAACCTTTAT CGATAACTAC TCTCAGATTG CCATCGACTT TGGGAAGACC
910 920 930 940 950 960
AACTCAGGCT ACATCAAGCT GGGTACCAGG TATGGCGGTA TCGATTGTTA CGGTATCAGC
970 980 990 1000 1010 1020
GCGGATACGG TCCCGGAGAT TGTGCGACTT TATACTGGAC TTGTTGGGCG TTCGAAGTTG
1030 1040 1050 1060 1070 1080
AAGCCCAGGT ATATTCTCGG AGCCCACCAA GCTTGTTATG GATACCAGCA GGAAAGTGAC
1090 1100 1110 1120 1130 1140
TTGCATGCTG TTGTTCAGCA GTACCGTGAC ACCAAGTTTC CGCTTGATGG GTTGCATGTC
1150 1160 1170 1180 1190 1200
GATGTCGACT TTCAGGACAA TTTCAGAACG TTTACCACTA ACCCGATTAC GTTCCCTAAT
1210 1220 1230 1240 1250 1260
CCCAAAGAAA TGTTTACCAA TCTAAGGAAC AATGGAATCA AGTGTTCCAC CAACATCACC
1270 1280 1290 1300 1310 1320

FIG. 10(I)

```
CCTGTTATCA GTATCAGAGA TCGCCCGAAT GGGTACAGTA CCCTCAATGA GGGATATGAT
      1330       1340       1350       1360       1370       1380
AAAAAGTACT TCATCATGGA TGACAGATAT ACCGAGGGGA CAAGTGGGGA CCCGCAAAAT
      1390       1400       1410       1420       1430       1440
GTTCGATACT CTTTTTACGG CGGTGGGAAC CCGGTTGAGG TTAACCCTAA TGATGTTTGG
      1450       1460       1470       1480       1490       1500
GCTCGGCCAG ACTTTGGAGA CAATTATGAC TTCCCTACGA ACTTCAACTG CAAAGACTAC
      1510       1520       1530       1540       1550       1560
CCCTATCATG GTGGTGTGAG TTACGGATAT GGGAATGGCA CTCCAGGTTA CTACCCTGAC
      1570       1580       1590       1600       1610       1620
CTTAACAGAG AGGAGGTTCG TATCTGGTGG GGATTGCAGT ACGAGTATCT CTTCAATATG
      1630       1640       1650       1660       1670       1680
GGACTAGAGT TTGTATGGCA AGATATGACA ACCCCAGCGA TCCATTCATC ATATGGAGAC
      1690       1700       1710       1720       1730       1740
ATGAAAGGGT TGCCCACCCG TCTGCTCGTC ACCGCCGACT CAGTTACCAA TGCCTCTGAG
      1750       1760       1770       1780       1790       1800
AAAAAGCTCG CAATTGAAAG TTGGGCTCTT TACTCCTACA ACCTCCATAA AGCAACCTTC
      1810       1820       1830       1840       1850       1860
CACGGTCTTG GTCGTCTTGA GTCTCGTAAG AACAAACGTA ACTTCATCCT CGGACGTGGT
      1870       1880       1890       1900       1910       1920
AGTTACGCCG GTGCCTATCG TTTTGCTGGT CTCTGGACTG GAGATAACGC AAGTACGTGG
      1930       1940       1950       1960       1970       1980
GAATTCTGGA AGATTTCGGT CTCCCAAGTT CTTTCTCTAG GTCTCAATGG TGTGTGTATA
      1990       2000       2010       2020       2030       2040
GCGGGGTCTG ATACGGGTGG TTTTGAGCCC GCACGTACTG AGATTGGGGA GGAGAAATAT
      2050       2060       2070       2080       2090       2100
TGCAGTCCGG AGCTACTCAT CAGGTGGTAT ACTGGATCAT TCCTTTTGCC ATGGCTTAGA
      2110       2120       2130       2140       2150       2160
AACCACTACG TCAAGAAGGA CAGGAAATGG TTCCAGGAAC CATACGCGTA CCCCAAGCAT
      2170       2180       2190       2200       2210       2220
CTTGAAACCC ATCCAGAGCT CGCAGATCAA GCATGGCTTT ACAAATCTGT TCTAGAAATT
      2230       2240       2250       2260       2270       2280
TGCAGATACT GGGTAGAGCT AAGATATTCC CTCATCCAGC TCCTTTACGA CTGCATGTTC
      2290       2300       2310       2320       2330       2340
CAAAACGTGG TCGATGGTAT GCCACTTGCC AGATCTATGC TCTTGACCGA TACTGAGGAT
      2350       2360       2370       2380       2390       2400
ACGACCTTCT TCAATGAGAG CCAAAAGTTC CTCGATAACC AATATATGGC TGGTGACGAC
      2410       2420       2430       2440       2450       2460
ATCCTTGTAG CACCCATCCT CCACAGCCGT AACGAGGTTC CGGGAGAGAA CAGAGATGTC
      2470       2480       2490       2500       2510       2520
TATCTCCCTC TATTCCACAC CTGGTACCCC TCAAACTTGA GACCGTGGGA CGATCAGGGA
      2530       2540       2550       2560       2570       2580
GTCGCTTTAG GGAATCCTGT CGAAGGTGGC AGCGTTATCA ACTACACTGC CAGGATTGTT
      2590       2600       2610       2620       2630       2640
GCCCCAGAGG ATTATAATCT CTTCCACAAC GTGGTGCCGG TCTACATCAG AGAGGGTGCC
      2650       2660       2670       2680       2690       2700
ATCATTCCGC AAATTCAGGT ACGCCAGTGG ATTGGCGAAG GAGGGCCTAA TCCCATCAAG
      2710       2720       2730       2740       2750       2760
TTCAATATCT ACCCTGGAAA GGACAAGGAG TATGTGACGT ACCTTGATGA TGGTGTTAGC
      2770       2780       2790       2800       2810       2820
CGCGATAGTG CACCAGATGA CCTCCCGCAG TACCGCGAGG CCTATGAGCA AGCGAAGGTC
      2830       2840       2850       2860       2870       2880
```

FIG. 10(II)

```
GAAGGCAAAG ACGTCCAGAA GCAACTTGCG GTCATTCAAG GGAATAAGAC TAATGACTTC
      2890       2900       2910       2920       2930       2940
TCCGCCTCCG GGATTGATAA GGAGGCAAAG GGTTATCACC GCAAAGTTTC TATCAAACAG
      2950       2960       2970       2980       2990       3000
GAGTCAAAAG ACAAGACCCG TACTGTCACC ATTGAGCCAA AACACAACGG ATACGACCCC
      3010       3020       3030       3040       3050       3060
TCTAAGGAAG TTGGTAATTA TTATACCATC ATTCTTTGGT ACGCACCGGG CTTTGACGGC
      3070       3080       3090       3100       3110       3120
AGCATCGTCG ATGTGAGCCA GGCGACCGTG AACATCGAGG GCGGGGTGGA ATGCGAAATT
      3130       3140       3150       3160       3170       3180
TTCAAGAACA CCGGCTTGCA TACGGTTGTA GTCAACGTGA AAGAGGTGAT CGGTACCACA
      3190       3200       3210
AAGTCCGTCA AGATCACTTG CACTACCGCT TAG
```

FIG. 10(III)

SEQUENCE LISTING

```
<160> NUMBER OF SEQ ID NOS: 16

<210> SEQ ID NO 1
<211> LENGTH: 223
<212> TYPE: PRT
<213> ORGANISM: Aspergillus niger

<400> SEQUENCE: 1

Gln Thr Met Cys Ser Gln Tyr Asp Ser Ala Ser Ser Pro Pro Tyr Ser
  1               5                  10                  15

Val Asn Gln Asn Leu Trp Gly Glu Tyr Gln Gly Thr Gly Ser Gln Cys
             20                  25                  30

Val Tyr Val Asp Lys Leu Ser Ser Ser Gly Ala Ser Trp His Thr Lys
         35                  40                  45

Trp Thr Trp Ser Gly Gly Glu Gly Thr Val Lys Ser Tyr Ser Asn Ser
```

-continued

```
     50                  55                  60

Gly Leu Thr Phe Asp Lys Lys Leu Val Ser Asp Val Ser Ser Ile Pro
 65                  70                  75                  80

Thr Ser Val Thr Trp Ser Gln Asp Asp Thr Asn Val Gln Ala Asp Val
                 85                  90                  95

Ser Tyr Asp Leu Phe Thr Ala Ala Asn Ala Asp His Ala Thr Ser Ser
            100                 105                 110

Gly Asp Tyr Glu Leu Met Ile Trp Leu Ala Arg Tyr Gly Ser Val Gln
        115                 120                 125

Pro Ile Gly Lys Gln Ile Ala Thr Ala Thr Val Gly Gly Lys Ser Trp
    130                 135                 140

Glu Val Trp Tyr Gly Thr Ser Thr Gln Ala Gly Ala Glu Gln Lys Thr
145                 150                 155                 160

Tyr Ser Phe Val Ala Gly Ser Pro Ile Asn Ser Trp Ser Gly Asp Ile
                165                 170                 175

Lys Asp Phe Phe Asn Tyr Leu Thr Gln Asn Gln Gly Phe Pro Ala Ser
            180                 185                 190

Ser Gln His Leu Ile Thr Leu Gln Phe Gly Thr Glu Pro Phe Thr Gly
        195                 200                 205

Gly Pro Ala Thr Phe Thr Val Asp Asn Trp Thr Ala Ser Val Asn
    210                 215                 220
```

<210> SEQ ID NO 2
<211> LENGTH: 669
<212> TYPE: DNA
<213> ORGANISM: Aspergillus niger

<400> SEQUENCE: 2

```
cagacgatgt gctctcagta tgacagtgcc tcgagccccc catactcggt gaaccagaac     60

ctctggggcg aataccaggg cactggcagc cagtgtgtct acgtcgacaa gcttagcagc    120

agtggtgcct catggcatac caaatggacc tggagtggtg gcgagggaac agtgaaaagc    180

tactctaact ccggccttac gtttgacaag aagctagtca gcgatgtgtc aagcattccc    240

acctcggtga catggagcca ggacgacacc aatgtccaag ccgatgtctc atatgatctg    300

ttcaccgcgg cgaatgcgga tcatgccact tccagcggtg actatgagct tatgatttgg    360

cttgcccgct acggctcagt ccagcctatt ggcaagcaga ttgccacggc cactgtggga    420

ggcaagtcct gggaggtgtg gtatggtacc agcacccagg ccggtgcgga gcaaaagaca    480

tatagcttcg tggcaggatc tcctatcaac tcgtggagtg gggacattaa ggacttcttc    540

aactatctca cccagaacca aggcttcccg gctagctctc agcatttgat cactctgcaa    600

tttggaactg agccgttcac cggtggcccg gcaaccttca cggttgacaa ctggaccgct    660

agtgtcaac                                                           669
```

<210> SEQ ID NO 3
<211> LENGTH: 1020
<212> TYPE: DNA
<213> ORGANISM: Aspergillus niger

<400> SEQUENCE: 3

```
aattgaagca ttttgatagg tttaagccta atcaggatat tggatgagtc gagttgcaga     60

agttgaggac ggtgggtgaa atcgggggtt tgataggtag gcaatgcagg gcggaacggg    120

aagggtctag acaatttctt tcttttggac agctggtgcg tttcactgag attaatagta    180

agcaaactac tcgctcgaag tcgtagatgt gcataatgga taactacagc caaccgaaat    240
```

-continued

```
ctccgggcag aaggcctgga ggcaggagga aacgtggata agagagtaat gtttgagtat    300

agatatgtag gcaagaaagg actgggagga aggaagtatc gcaaacaaga caagtcactg    360

aataggaaag aatggggcca tcagagaaat gaatctaaac ggtaactgca gatattacat    420

ggaagaaaat actatgatcc ctaattgata tggttccatg gcccctggag acttaaacct    480

cgtggtatga taaacatatg agttacattc tcggtaaatc caacattact cccaagctct    540

gttgatattc tccgataatt caccgataac caaccaacct actcccgtct agatccaatt    600

ggtctatatg cataatggat atcgtcagca caggcagaac cctttaattt atttctggag    660

atcccgttct ccacaatgct tggttgccga ctgccacaga ccatcgctaa cttgaagcgg    720

aaagtgctcc gatgaagggt ctcattttga aacggaggat ttacatgtca atgttgcagg    780

ctggcgttga tgatggcgca acctgctata gctagttggc ttacttcgtc ctggctgccg    840

tattggacac ggaaagtcgg acaataatag tgttaacagt aagcgccatt gatcagagtt    900

gatgtattta aagctgcgtc gtctgctgcc ccctccgtgt tcgtgtctta ttccaaacat    960

tcaacctcta ttcctttcga agtcctttag atctgccgtt cctctgcttt attgcccaac   1020
```

```
<210> SEQ ID NO 4
<211> LENGTH: 17
<212> TYPE: PRT
<213> ORGANISM: Aspergillus niger

<400> SEQUENCE: 4

Ser Trp Glu Val Trp Tyr Gly Thr Ser Thr Gln Ala Gly Ala Glu Gln
  1               5                  10                  15

Lys


<210> SEQ ID NO 5
<211> LENGTH: 10
<212> TYPE: PRT
<213> ORGANISM: Aspergillus niger

<400> SEQUENCE: 5

Thr Tyr Ser Phe Val Ala Gly Ser Pro Ile
  1               5                  10


<210> SEQ ID NO 6
<211> LENGTH: 35
<212> TYPE: PRT
<213> ORGANISM: Aspergillus niger
<220> FEATURE:
<221> NAME/KEY: UNSURE
<222> LOCATION: (15)..(29)
<223> OTHER INFORMATION: Xaa at the locations above represents any amino
      acid

<400> SEQUENCE: 6

Lys Leu Val Ser Asp Val Ser Ser Ile Pro Thr Ser Val Thr Xaa Ser
  1               5                  10                  15

Gln Asp Asp Thr Asn Xaa Xaa Ala Ala Val Ser Tyr Xaa Leu Phe Thr
             20                  25                  30

Ala Ala Asn
         35


<210> SEQ ID NO 7
<211> LENGTH: 11
<212> TYPE: PRT
<213> ORGANISM: Aspergillus niger
```

-continued

<400> SEQUENCE: 7

```
Trp Thr Trp Ser Gly Gly Glu Gly Thr Val Lys
  1               5                  10
```

<210> SEQ ID NO 8
<211> LENGTH: 11
<212> TYPE: PRT
<213> ORGANISM: Aspergillus niger

<400> SEQUENCE: 8

```
Leu Ser Ser Ser Gly Ala Ser Trp His Thr Lys
  1               5                  10
```

<210> SEQ ID NO 9
<211> LENGTH: 20
<212> TYPE: DNA
<213> ORGANISM: Aspergillus niger
<220> FEATURE:
<221> NAME/KEY: unsure
<222> LOCATION: (3)..(12)
<223> OTHER INFORMATION: n at the locations above is any nucleic acid

<400> SEQUENCE: 9

```
gtnccrtacc anacytccca                                                20
```

<210> SEQ ID NO 10
<211> LENGTH: 17
<212> TYPE: DNA
<213> ORGANISM: Aspergillus niger
<220> FEATURE:
<221> NAME/KEY: unsure
<222> LOCATION: (6)..(15)
<223> OTHER INFORMATION: n at the locations above is any nucleic acid

<400> SEQUENCE: 10

```
tggacntggw snggngg                                                   17
```

<210> SEQ ID NO 11
<211> LENGTH: 345
<212> TYPE: DNA
<213> ORGANISM: Aspergillus niger

<400> SEQUENCE: 11

```
gtggagtggt ggcgagggaa cagtgaaaag ctactctaac tcggscctta cgtttgacaa     60

gaagctagtc agcgatgtgt caagcattcc cacctcggtg acatggagcc aggacgacac    120

caatgtccaa gccgatgtct catatgatct gttcaccgcg gcgaatgcgg atcatgccac    180

ttccagcggt gactatgagc ttatgatttg gtatgtgacg tcgtgaacaa gatagatgga    240

ggaggctaac gtaaccaggc ttgcccgcta cggctcagtc cagcctattg gcaagcagat    300

tgccacggcc actgtgggag gcaagtcctg ggaggtctgg tacgg                    345
```

<210> SEQ ID NO 12
<211> LENGTH: 2360
<212> TYPE: DNA
<213> ORGANISM: Aspergillus niger

<400> SEQUENCE: 12

```
aattgaagca ttttgatagg tttaagccta atcaggatat tggatgagtc gagttgcaga     60

agttgaggac ggtgggtgaa atcgggggtt tgataggtag gcaatgcagg gcggaacggg    120

aagggtctag acaatttctt tcttttggac agctggtgcg tttcactgag attaatagta    180

agcaaactac tcgctcgaag tcgtagatgt gcataatgga taactacagc caaccgaaat    240
```

-continued

```
ctccgggcag aaggcctgga ggcaggagga aacgtggata agagagtaat gtttgagtat    300
agatatgtag gcaagaaagg actgggagga aggaagtatc gcaaacaaga caagtcactg    360
aataggaaag aatggggcca tcagagaaat gaatctaaac ggtaactgca gatattacat    420
ggaagaaaat actatgatcc ctaattgata tggttccatg gcccctggag acttaaacct    480
cgtggtatga taaacatatg agttacattc tcggtaaatc caacattact cccaagctct    540
gttgatattc tccgataatt caccgataac caaccaacct actcccgtct agatccaatt    600
ggtctatatg cataatggat atcgtcagca caggcagaac cctttaattt atttctggag    660
atcccgttct ccacaatgct tggttgccga ctgccacaga ccatcgctaa cttgaagcgg    720
aaagtgctcc gatgaagggt ctcattttga aacggaggat ttacatgtca atgttgcagg    780
ctggcgttga tgatggcgca acctgctata gctagttggc ttacttcgtc ctggctgccg    840
tattggacac ggaaagtcgg acaataatag tgttaacagt aagcgccatt gatcagagtt    900
gatgtattta aagctgcgtc gtctgctgcc ccctccgtgt tcgtgtctta ttccaaacat    960
tcaacctcta ttcctttcga agtcctttag atctgccgtt cctctgcttt attgcccaac   1020
atgaagctct ccatgacact ttccctgttt gcggccactg ccatgggcca gacgatgtgc   1080
tctcagtatg acagtgcctc gagcccccca tactcggtga accagaacct ctggggcgaa   1140
taccagggca ctggcagcca gtgtgtctac gtcgacaagc ttagcagcag tggtgcctca   1200
tggcatacca aatggacctg gagtggtggc gagggaacag tgaaaagcta ctctaactcc   1260
ggccttacgt ttgacaagaa gctagtcagc gatgtgtcaa gcattcccac ctcggtgaca   1320
tggagccagg acgacaccaa tgtccaagcc gatgtctcat atgatctgtt caccgcggcg   1380
aatgcggatc atgccacttc cagcggtgac tatgagctta tgatttggta tgtgacgtcg   1440
tgaacaagat agatggagga ggctaacgta accaggcttg cccgctacgg ctcagtccag   1500
cctattggca agcagattgc cacggccact gtgggaggca agtcctggga ggtgtggtat   1560
ggtaccagca cccaggccgg tgcggagcaa aagacatata gcttcgtggc aggatctcct   1620
atcaactcgt ggagtgggga cattaaggac ttcttcaact atctcaccca gaaccaaggc   1680
ttcccggcta gctctcagca tttgatcagt gagttttcct aattctacta gcgagcgccg   1740
gcagttgaaa ttggtcacta acagaagtga tgattagctc tgcaatttgg aactgagccg   1800
ttcaccggtg gcccggcaac cttcacggtt gacaactgga ccgctagtgt caactaaaag   1860
gctttaggcg cggctggggt aaataacagc ttgtttcttc gttctagaac gtcgggcgtg   1920
taagagctag aaatccaccc actctgattg gaaacactca ttcaagatcg gtactcctct   1980
tcagccgaga aaggcacaga tagtgtatcg aatccaatca aatctatttg gtgttgctta   2040
aattccgagc cagtcctttc cttgaaaggt aatccacccg tagcgattga tcattaacag   2100
atccgagtgg tgctaggtta aattgctaac ccgatcccgc tccaattagc tagcgcatcc   2160
ggcagattca aacttgacag tgggccgggc attacctgaa cctgtagaag gaacagaccc   2220
ttgtctagaa atctctaaat agtataagcc gaaacttgcc ccggacgtac cctaagctaa   2280
gattgctctt cgcattccca ggggggtgaa ctctctaaag agggagcatc gcttgccgat   2340
gtctggttcg ggatcatga                                                2360
```

<210> SEQ ID NO 13
<211> LENGTH: 239
<212> TYPE: PRT
<213> ORGANISM: Aspergillus niger -continued

<400> SEQUENCE: 13

```
Met Lys Leu Ser Met Thr Leu Ser Leu Phe Ala Ala Thr Ala Met Gly
  1               5                  10                  15

Gln Thr Met Cys Ser Gln Tyr Asp Ser Ala Ser Ser Pro Pro Tyr Ser
             20                  25                  30

Val Asn Gln Asn Leu Trp Gly Glu Tyr Gln Gly Thr Gly Ser Gln Cys
         35                  40                  45

Val Tyr Val Asp Lys Leu Ser Ser Ser Gly Ala Ser Trp His Thr Lys
     50                  55                  60

Trp Thr Trp Ser Gly Gly Glu Gly Thr Val Lys Ser Tyr Ser Asn Ser
 65                  70                  75                  80

Gly Leu Thr Phe Asp Lys Lys Leu Val Ser Asp Val Ser Ser Ile Pro
                 85                  90                  95

Thr Ser Val Thr Trp Ser Gln Asp Asp Thr Asn Val Gln Ala Asp Val
            100                 105                 110

Ser Tyr Asp Leu Phe Thr Ala Ala Asn Ala Asp His Ala Thr Ser Ser
        115                 120                 125

Gly Asp Tyr Glu Leu Met Ile Trp Leu Ala Arg Tyr Gly Ser Val Gln
    130                 135                 140

Pro Ile Gly Lys Gln Ile Ala Thr Ala Thr Val Gly Gly Lys Ser Trp
145                 150                 155                 160

Glu Val Trp Tyr Gly Thr Ser Thr Gln Ala Gly Ala Glu Gln Lys Thr
                165                 170                 175

Tyr Ser Phe Val Ala Gly Ser Pro Ile Asn Ser Trp Ser Gly Asp Ile
            180                 185                 190

Lys Asp Phe Phe Asn Tyr Leu Thr Gln Asn Gln Gly Phe Pro Ala Ser
        195                 200                 205

Ser Gln His Leu Ile Thr Leu Gln Phe Gly Thr Glu Pro Phe Thr Gly
    210                 215                 220

Gly Pro Ala Thr Phe Thr Val Asp Asn Trp Thr Ala Ser Val Asn
225                 230                 235
```

<210> SEQ ID NO 14
<211> LENGTH: 503
<212> TYPE: DNA
<213> ORGANISM: Aspergillus niger

<400> SEQUENCE: 14

```
aaggctttag gcgcggctgg ggtaaataac agcttgtttc ttcgttctag aacgtcgggc     60

gtgtaagagc tagaaatcca cccactctga ttggaaacac tcattcaaga tcggtactcc    120

tcttcagccg agaaaggcac agatagtgta tcgaatccaa tcaaatctat ttggtgttgc    180

ttaaattccg agccagtcct ttccttgaaa ggtaatccac ccgtagcgat tgatcattaa    240

cagatccgag tggtgctagg ttaaattgct aacccgatcc cgctccaatt agctagcgca    300

tccggcagat tcaaacttga cagtgggccg ggcattacct gaacctgtag aaggaacaga    360

cccttgtcta gaaatctcta aatagtataa gccgaaactt gccccggacg taccctaagc    420

taagattgct cttcgcattc ccaggggggt gaactctcta aagagggagc atcgcttgcc    480

gatgtctggt tcggggatca tga                                            503
```

<210> SEQ ID NO 15
<211> LENGTH: 48
<212> TYPE: DNA
<213> ORGANISM: Aspergillus niger -continued

```
<400> SEQUENCE: 15

atgaagctct ccatgacact ttccctgttt gcggccactg ccatgggc              48


<210> SEQ ID NO 16
<211> LENGTH: 16
<212> TYPE: PRT
<213> ORGANISM: Aspergillus niger

<400> SEQUENCE: 16

Met Lys Leu Ser Met Thr Leu Ser Leu Phe Ala Ala Thr Ala Met Gly
  1               5                  10                  15
```

ENDO β-1,4-GLUCANASE FROM ASPERGILLUS

RELATED APPLICATIONS

This application is the National Phase of PCT/EP96/01008, filed Mar. 11, 1996 and designating the U.S. and claiming priority from U.K. application 9505475.5, filed Mar. 17, 1995.

FIELD OF THE INVENTION

The present invention relates to an enzyme. In addition, the present invention relates to a nucleotide sequence coding for the enzyme. Also, the present invention relates to a promoter, wherein the promoter can be used to control the expression of the nucleotide sequence coding for the enzyme.

In particular, the enzyme of the present invention is a glucanase enzyme—i.e. an enzyme that can degrade β-1,4-glucosidic bonds.

BACKGROUND OF THE INVENTION

It is known that it is desirable to direct expression of a gene of interest ("GOI") in certain tissues of an organism—such as a filamentous fungus (such as *Aspergillus niger*) or even a plant crop. The resultant protein or enzyme may be useful for the organism itself. For example, it may be desirable to produce crop protein products with an optimised amino acid composition and so increase the nutritive value of a crop. For example, the crop may be made more useful as a feed. In the alternative, it may be desirable to isolate the resultant protein or enzyme and then use the protein or enzyme to prepare, for example, food compositions. In this regard, the resultant protein or enzyme can be a component of the food composition or it can be used to prepare food compositions, including altering the characteristics or appearance of food compositions.

It may even be desirable to use the organism, such as a filamentous fungus or a crop plant, to express non-plant genes, such as for the same purposes.

Also, it may be desirable to use an organism, such as a filamentous fungus or a crop plant, to express mammalian genes. Examples of the latter products include interferons, insulin, blood factors and plasminogen activators.

It is also desirable to use micro-organisms, such as filamentous fungi, to prepare products from GOIs by use of promoters that are active in the micro-organisms.

Fruit and vegetable cell walls largely consist of polysaccharide, the major components being pectin, cellulose and xyloglucan, R. R. Selvendran and J. A. Robertson, IFR Report 1989. Numerous cell wall models have been proposed which attempt to incorporate the essential properties of strength and flexibility (P. Albersheim, Sci. Am. 232, 81–95, 1975;, P. Albersheim, Plant Biochem. 3rd Edition (Bonner and Varner), Ac. Press, 1976; T. Hayashi, Ann. Rev. Plant Physiol. & Plant Mol. Biol., 40, 139–168, 1989).

The composition of the plant cell wall is complex and variable. Polysaccharides are mainly found in the form of long chains of cellulose (the main structural component of the plant cell wall), hemicellulose (comprising various β-xylan chains, such as xyloglucans) and pectic substances (consisting of galacturonans and rhamnogalacturonans; arabinans; and galactans and arabinogalactans).

In particular, glucans are polysaccharides made up exclusively of glucose subunits. Typical examples of glucans are starch and cellulose.

The enzymes that degrade glucans are collectively referred to as glucanases. A typical glucanase is β-1,4-endoglucanase.

β-1,4-endoglucanases have uses in many industries. For example, in the brewing industry, barley is used for production of malt, and, in the latter years, as adjunct in the brewing process. When the quality of the malt is poor, or barley has been used as an adjunct, problems with high viscosity in the wort can arise because of β-glucans from the barley. In this regard, barley contains large quantities of mixed β-1,3/1,4-glucans of very high molecular weight. When dissolved, these glucans produce high viscosity solutions, which can cause troubles in some applications. For example, the high viscosity reduces the filterability of the wort and can lead to unacceptable long filtration times. To avoid these problems β-glucanase has been traditionally added to wort to avoid such problems—i.e. the problem with glucans can be avoided by addition of enzymes, in particular, glucanases, which degrade the polymers.

Further information on these problems may be found in the Grindsted brochure called "Glucanase GV", the reviews by Dr. C. W. Bamforth (Brewers Digest June 1982 pages 22–28; and Brewers' Guardian September 1985 pages 21–26), and the paper by T. Godfrey (Industrial Enzymology The Application of Enzymes in Industry Chapter 4.5 pages 221–259).

In the feed industry barley can be used for chicken feed because it is cheap, but again the β-glucan can give problems for the digestion of the chicken. By addition of β-glucanase to the feed the digestibility of the feed can be increased. In addition, the faeces of chickens feeding on feed containing barley is sticky making it difficult to remove and results in dirty eggs.

WO 93/2019 discusses endo-β-1,4-glucanases (EC no. 3.2.1.4). According to WO 93/2019, these glucanases are a group of hydrolases which catalyse endo hydrolysis of 1,4-β-D-glycosidic linkages in cellulose, lichenin, cereal β-D-glucans and other plant material containing cellulosic parts. Endo-1,4-β-D-glucan 4-glucano hydrolase is sometimes called endo-β-1,4-glucanase.

The endo-β-1,4-glucanase of WO 93/2019 exhibits a pH-optimum of 2.0 to 4.0, an isoelectric point of 2.0 to 3.5, a molecular weight of between 30,000 and 50,000, and a temperature optimum between 30 and 70° C.

Further teachings on glucans may be found in WO 93/17101, in particular xyloglucans. According to WO 93/17101 the xyloglucans are 1,4-β-glucans that have been extensively substituted with α-1,6-xylosyl side chains, some of which are 1,2-β-galactosylated. They are found in large amounts in the primary cell walls of dicots but also in certain seeds, where they serve different roles. Primary cell wall xyloglucan is fucosylated. Xyloglucan is tightly hydrogen bonded to cellulose microfibrils and requires concentrated alkali or strong swelling agents to release it. Xyloglucan is thought to form cross-bridoes between cellulose microfibrils, the cellulose/xyloglucan network forming the major load-bearing/elastic network of the wall. DCB mutated suspension culture cells (cell walls lacking cellulose) release xyloglucan into their media, suggesting that xyloglucan is normally rightly bound to cellulose.

Hydrolysis of primary cell wall xyloglucan has been demonstrated in segments of dark grown squash hypocotyls, during IAA induced growth (K. Wakabayashi et al, Plant Physiol., 95, 1070–1076, 1991). Endohydrolysis of wall xyloglucan is thought to contribute to wall loosening which accompanies cell expansion (T. Hyashi, Ann. Rev. Plant Physiol. & Plant Mol. Biol., 40, 139–168, 1989). The average molecular weight of xyloglucan has also been shown to decrease during tomato fruit ripening and this may contribute to the tissue softening which accompanies the ripening process (D. J. Huber, J. Amer. Soc. Hort. Sci., 108(3), 405–409, 1983). Certain seeds, e.g. Nasturtium, contain up to 30% by weight of xyloglucan, stored in thickened cotyledonary cell walls, which serves as a reserve polysaccharide and is rapidly depolymerised during germination.

It would be useful to increase glucanase activity, for example to have a plant with high concentration of glucanase for use in feed, preferably using recombinant DNA techniques.

OBJECTS AND SUMMARY OF THE INVENTION

The present invention seeks to provide an enzyme having glucanase activity; preferably wherein the enzyme can be prepared in certain or specific cells or tissues, such as in just a specific cell or tissue, of an organism, typically a filamentous fungus, preferably of the genus Aspergillus, such as *Aspergillus niger*, or even a plant.

Also, the present invention seeks to provide a GOI coding for the enzyme that can be expressed preferably in specific cells or tissues, such as in certain or specific cells or tissues, of an organism, typically a filamentous fungus, preferably of the genus Aspergillus, such as *Aspergillus niger*, or even a plant.

In addition, the present invention seeks to provide a promoter that is capable of directing expression of a GOI, such as a nucleotide sequence coding for the enzyme according to the present invention, preferably in certain specific cells or tissues, such as in just a specific cell or tissue, of an organism, typically a filamentous fungus, preferably of the genus Aspergillus, such as *Aspergillus niger*, or even a plant. Preferably, the promoter is used in Aspergillus wherein the product encoded by the GOI is excreted from the host organism into the surrounding medium.

Furthermore, the present invention seeks to provide constructs, vectors, plasmids, cells, tissues, organs and organisms comprising the GOI and/or the promoter, and methods of expressing the same, preferably in specific cells or tissues, such as expression in just a specific cell or tissue, of an organism, typically a filamentous fungus, preferably of the genus Aspergillus, or even a plant.

According to a first aspect of the present invention there is provided an enzyme obtainable from Aspergillus, wherein the enzyme has the following characteristics: a MW of 24,235 D±50 D; a pI value of about 4; glucanase activity; and wherein the glucanase activity is endo β-1,4-glucanase activity.

According to a second aspect of the present invention there is provided an enzyme having the sequence shown as SEQ. I.D. No. 1 or a variant, homologue or fragment thereof.

According to a third aspect of the present invention there is provided an enzyme coded by the nucleotide sequence shown as SEQ. I.D. No. 2 or a variant, homologue or fragment thereof or a sequence complementary thereto.

According to a fourth aspect of the present invention there is provided a nucleotide sequence coding for the enzyme according to the present invention.

According to a fifth aspect of the present invention there is provided a nucleotide sequence having the sequence shown as SEQ. I.D. No. 2 or a variant, homologue or fragment thereof or a sequence complementary thereto.

According to a sixth aspect of the present invention there is provided a promoter having the sequence shown as SEQ. I.D. No. 3 or a variant. homologue or fragment thereof or a sequence complementary thereto.

According to a seventh aspect of the present invention there is provided a terminator having the nucleotide sequence shown as SEQ. I.D. No. 14 or a variant, homologue or fragment thereof or a sequence complementary thereto.

According to an eighth aspect of the present invention there is provided a signal sequence having the nucleotide sequence shown as SEQ. I.D. No. 15 or a variant, homologue or fragment thereof or a sequence complementary thereto.

According to a ninth aspect of the present invention there is provided a process for expressing a GOI by use of a promoter, wherein the promoter is the promoter according to the present invention.

According to a tenth aspect of the present invention there is provided the use of an enzyme according to the present invention to degrade a glucan.

According to an eleventh aspect of the present invention there is provided plasmid NCIMB 40704, or a nucleotide sequence obtainable therefrom for expressing an enzyme capable of degrading arabinoxylan or for controlling the expression thereof or for controlling the expression of another GOI.

According to a twelfth aspect of the present invention there is provided a signal sequence having the sequence shown as SEQ. I.D. No. 16 or a variant, homologue or fragment thereof.

According to a thirteenth aspect of the present invention there is provided a glucanase enzyme having the ability to degrade β-1,4-glucosidic bonds, which is immunologically reactive with an antibody raised against a purified glucanase enzyme having the sequence shown as SEQ. I.D. No. 1.

According to a fourteenth aspect of the present invention there is provided a promoter that is inducible by glucose.

According to a fifteenth aspect of the present invention there is provided the use of glucose to induce a promoter.

Other aspects of the present invention include constructs, vectors, plasmids, cells, tissues, organs and transgenic organisms comprising the aforementioned aspects of the present invention.

Other aspects of the present invention include methods of expressing or allowing expression or transforming any one of the nucleotide sequence, the construct, the plasmid, the vector, the cell, the tissue, the organ or the organism, as well as the products thereof.

Additional aspects of the present invention include uses of the promoter for expressing GOIs in culture media such as a broth or in a transgenic organism.

Further aspects of the present invention include uses of the enzyme for preparing or treating foodstuffs, including animal feed.

In the following text, the enzyme of the present invention is sometimes referred to as Egla enzyme and the coding sequence therefor is sometimes referred to as the Egla gene In addition, the promoter of the present invention is sometimes referred to as Egla promoter.

Preferably the enzyme is coded by the nucleotide sequence shown as SEQ. I.D. No. 2 or a variant, homologue or fragment thereof or a sequence complementary thereto.

Preferably the nucleotide sequence has the sequence shown as SEQ. I.D. No. 2 or a variant, homologue or fragment thereof or a sequence complementary thereto.

Preferably the nucleotide sequence is operatively linked to a promoter.

Preferably the promoter is the promoter having the sequence shown as SEQ. I.D. No. 3 or a variant, homologue or fragment thereof or a sequence complementary thereto.

Preferably the promoter of the present invention is operatively linked to a GOI.

Preferably the GOI comprises a nucleotide sequence according to the present invention.

In one preferred embodiment, the transgenic organism is a fungus. For example the organism can be a yeast, which would then be useful in for example the brewing industry.

Preferably the transgenic organism is a filamentous fungus, more preferably of the genus Aspergillus.

In another preferred embodiment the transgenic organism is a plant.

In another preferred embodiment the transgenic organism is a yeast. In this regard, yeast have been widely used as a vehicle for heterologous gene expression. The species *Saccharomyces cerevisiae* has a long history of industrial use, including use for heterologous gene expression. Expression of heterologous genes in *Saccharomyces cerevisiae* has been reviewed by Goodey et at (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

An additional advantage is that yeasts are capable of post-translational modifications of proteins and thereby have the potential for glycosylation and/or secretion of heterologous gene products into the growth medium. A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

The glycosylation of enzymes expressed in yeast is known to increase heat stability of the enzyme. Enhancing the heat stability of the glucanase according to the present invention will make this enzyme suitable for use in the brewing industry and for use in the preparation of animal feed, i.e. chicken feed.

Yeasts are known to secrete very few proteins into the culture medium. This makes yeast a very attractive host for expression of heterologous genes, since secretable gene products can easily be recovered and purified.

Several types of yeast vectors are available, including integrative vectors, which require recombination with the host genome for their maintenance, and autonomously replicating plasmid vectors.

In order to prepare the transgenic Saccharomyces, expression constructs are prepared by inserting a GOI (such as an amylase or SEQ. ID No 2) into a construct designed for expression in yeast. Several types of constructs used for heterologous expression have been developed. The constructs contain a promoter active in yeast fused to the GOI, usually a promoter of yeast origin, such as the GAL1 promoter, is used. The GOI can be fused to a signal sequence which directs the protein encoded by the GOI to be secreted. Usually a signal sequence of yeast origin, such as the sequence encoding the SUC2 signal peptide, is used. A terminator active in yeast ends the expression system.

Heterologous expression in yeast has been reported for several genes. The gene products can be glycosylated which is advantageous for some enzymes intended for specific application where heat tolerance is desirable. The proteins can be deposited intracellularly if the GOI is not fused to a signal sequence, or they can be secreted extracelluarly if the GOI is equipped with a signal sequence.

For the transformation of yeast several transformation protocols have been developed.

For example, the transgenic Saccharomyces according to the present invention can be prepared by following the teachings of Hinnen et al (1978, Proceedings of the National Academy of Sciences of the USA 75, 1929) Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Highly preferred embodiments of each of the aspects of the present invention do not include any one of the native enzyme, the native promoter or the native nucleotide sequence in its natural environment.

Preferably, in any one of the plasmid, the vector such as an expression vector or a transformation vector, the cell, the tissue, the organ, the organism or the transgenic organism, the promoter is present in combination with at least one GOI.

Preferably the promoter and the GOI are stably incorporated within the transgenic organism's genome.

Preferably the transgenic organism is a filamentous fungus, preferably of the genus Aspergillus, more preferably *Aspergillus niger*. Alternatively, the transgenic organism can be a yeast. The transgenic organism can even be a plant, such as a monocot or dicot plant.

A highly preferred embodiment is an enzyme obtainable from Aspergillus, wherein the enzyme has the following characteristics: a MW of 24,235 D±50 D; a pI value of about 4; glucanase activity; and wherein the glucanase activity is endo β-1,4-glucanase activity; wherein the enzyme has the sequence shown as SEQ. I.D. No. 1 or a variant, homologue or fragment thereof.

Another highly preferred embodiment is an enzyme obtainable from Aspergillus, wherein the enzyme has the following characteristics: a MW of 24,235 D±50 D; a pI value of about 4; glucanase activity; and wherein the glucanase activity is endo β-1,4-glucanase activity; wherein the enzyme is coded by the nucleotide sequence shown as SEQ. I.D. No. 2 or a variant, homologue or fragment thereof or a sequence complementary thereto.

The advantages of the present invention are that it provides a means for preparing a glucanase enzyme and the nucleotide sequence coding for the same. In addition, it provides a promoter that can control the expression of that, or another, nucleotide sequence.

Other advantages of the present invention are that the enzyme can be used to prepare useful feeds containing cereals, such as barley, maize, rice etc.

The present invention therefore provides an enzyme having glucanase activity wherein the enzyme can be prepared in certain or specific cells or tissues, such as in just a specific cell or tissue, of an organism, typically a filamentous fungus, preferably of the genus Aspergillus, such as *Aspergillus niger*. The enzyme may even be prepared in a plant.

Also, the present invention provides a GOI coding for the enzyme that can be expressed preferably in specific cells or tissues, such as in certain or specific cells or tissues, of an organism, typically a filamentous fungus, preferably of the genus Aspergillus, such as *Aspergillus niger*. The GOI may even be expressed in a plant.

In addition, the present invention provides a promoter that is capable of directing expression of a GOI, such as a nucleotide sequence coding for the enzyme according to the present invention, preferably in certain specific cells or tissues, such as in just a specific cell or tissue, of an organism, typically a filamentous fungus, preferably of the genus Aspergillus, such as *Aspergillus niger*, or even a plant. Preferably, the promoter is used in Aspergillus wherein the product encoded by the GOI is excreted from the host organism into the surrounding medium. The promoter may even be tailored (if necessary) to express a GOI in a plant.

The present invention also provides constructs, vectors, plasmids, cells, tissues, organs and organisms comprising the GOI and/or the promoter, and methods of expressing the same, preferably in specific cells or tissues, such as expression in just a specific cell or tissue, of an organism, typically a filamentous fungus, preferably of the genus Aspergillus, or even a plant.

DETAILED DESCRIPTION

The terms "variant", "homologue" or "fragment" in relation to the enzyme include any substitution of, variation of, modification of, replacement of, deletion of or addition of one (or more) amino acid from or to the sequence providing the resultant amino acid sequence has glucanase activity, preferably having at least the same activity of the enzyme shown in the sequence listings (SEQ I.D. No. 1 Nos. 12 and 13). In particular, the term "homologue" covers homology with respect to structure and/or function providing the resultant enzyme has glucanase activity. With respect to sequence homology, preferably there is at least 75%, more preferably at least 85%, more preferably at least 90% homology to SEQ ID NO. 1 shown in the attached sequence listings. More preferably there is at least 95%, more preferably at least 98%, homology to SEQ ID NO. 1 shown in the attached sequence listings.

The terms "variant", "homologue" or "fragment" in relation to the nucleotide sequence coding for the enzyme include any substitution of, variation of, modification of, replacement of, deletion of or addition of one (or more) nucleic acid from or to the sequence providing the resultant nucleotide sequence codes for an enzyme having glucanase activity, preferably having at least the same activity of the enzyme shown in the sequence listings (SEQ I.D. No. 2 or Nos. 12 and 13). In particular, the term "homologue" covers homology with respect to structure and/or function providing the resultant nucleotide sequence codes for an enzyme having glucanase activity. With respect to sequence homology, preferably there is at least 75%, more preferably at least 85%, more preferably at least 90% homology to SEQ ID NO. 2 shown in the attached sequence listings. More preferably there is at least 95%, more preferably at least 98%, homology to SEQ ID NO. 2 shown in the attached sequence listings.

The terms "variant", "homologue" or "fragment" in relation to the promoter include any substitution of, variation of, modification of, replacement of, deletion of or addition of one (or more) nucleic acid from or to the sequence providing the resultant nucleotide sequence has the ability to act as a promoter in an expression system—such as the transformed cell or the transgenic organism according to the present invention. In particular, the term "homologue" covers homology with respect to structure and/or function providing the resultant nucleotide sequence has the ability to act as a promoter. With respect to sequence homology, preferably there is at least 75%, more preferably at least 85%, more preferably at least 90% homology to SEQ ID NO. 3 shown in the attached sequence listings. More preferably there is at least 95%, more preferably at least 98%, homology to SEQ ID NO. 3 shown in the attached sequence listings.

The terms "variant", "homologue" or "fragment" in relation to the terminator or signal nucleotide sequences include any substitution of, variation of, modification of, replacement of, deletion of or addition of one (or more) nucleic acid from or to the sequence providing the resultant nucleotide sequence has the ability to act as a terminator or codes for an amino acid sequence that has the ability to act as a signal sequence respectively in an expression system—such as the transformed cell or the transgenic organism according to the present invention. In particular, the term "homologue" covers homology with respect to structure and/or function providing the resultant nucleotide sequence has the ability to act as or code for a terminator or signal respectively. With respect to sequence homology, preferably there is at least 75%, more preferably at least 85%, more preferably at least 90% homology to SEQ ID NO.s 14 and 15 (respectively) shown in the attached sequence listings. More preferably there is at least 95%, more preferably at least 98%, homology to SEQ ID NO.s 14 and 15 (respectively) shown in the attached sequence listings.

The terms "variant", "homologue" or "fragment" in relation to the signal amino acid sequence include any substitution of, variation of, modification of, replacement of, deletion of or addition of one (or more) amino acid from or to the sequence providing the resultant sequence has the ability to act as a signal sequence in an expression system—such as the transformed cell or the transgenic organism according to the present invention. In particular, the term "homologue" covers homology with respect to structure and/or function providing the resultant nucleotide sequence has the ability to act as or code for a signal. With respect to sequence homology, preferably there is at least 75%, more preferably at least 85%, more preferably at least 90% homology to SEQ ID NO 16 shown in the attached sequence listings. More preferably there is at least 95%, more preferably at least 98%, homology to SEQ ID NO 16 shown in the attached sequence listings.

The above terms are synonymous with allelic variations of the sequences.

The term "complementary" means that the present invention also covers nucleotide sequences that can hybridise to the nucleotide sequences of the coding sequence, the promoter sequence, the terminator sequence or the signal sequence respectively.

The term "nucleotide" in relation to the present invention includes genomic DNA, CDNA, synthetic DNA, and RNA. Preferably it means DNA, more preferably cDNA for the coding sequence of the present invention since the genomic coding sequence has two introns and their removal would allow expression in bacteria.

The term "construct"—which is synonymous with terms such as "conjugate", "cassette" and "hybrid"—includes a GOI directly or indirectly attached to a promoter. An example of an indirect attachment is the provision of a suitable spacer group such as an intron sequence, such as the Sh1-intron or the ADH intron, intermediate the promoter and the GOI. The same is true for the term "fused" in relation to the present invention which includes direct or indirect attachment. In each case, it is highly preferred that the terms do not cover the natural combination of the gene coding for the enzyme ordinarily associated with the wild type gene promoter and when they are both in their natural environment. A highly preferred embodiment is the or a GOI being operatively linked to a or the promoter.

The construct may even contain or express a marker which allows for the selection of the genetic construct in, for example, a filamentous fungus, preferably of the genus Aspergillus, such as *Aspergillus niger*, or plants, preferably cereals, such as maize, rice, barley etc., into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

The term "vector" includes expression vectors and transformation vectors.

The term "expression vector" means a construct capable of in vivo or in vitro expression.

The term "transformation vector" means a construct capable of being transferred from one species to another—such as from an *E. coli* plasmid to a filamentous fungus, preferably of the genus Aspergillus. It may even be a construct capable of being transferred from an *E. coli* plasmid to an Agrobacterium to a plant.

The term "tissue" includes tissue per se and organ.

The term "organism" in relation to the present invention includes any organism that could comprise the promoter according to the present invention and/or the nucleotide sequence coding for the enzyme according to the present invention and/or products obtained therefrom, wherein the promoter can allow expression of a GOI and/or wherein the nucleotide sequence according to the present invention can be expressed when present in the organism.

Preferably the organism is a filamentous fungus, preferably of the genus Aspergillus, more preferably *Aspergillus niger.*

The term "transgenic organism" in relation to the present invention includes any organism that comprises the promoter according to the present invention and/or the nucleotide sequence coding for the enzyme according to the present invention and/or products obtained therefrom, wherein the promoter can allow expression of a GOI and/or wherein the nucleotide sequence according to the present invention can be expressed within the organism. Preferably the promoter and/or the nucleotide sequence is (are) incorporated in the genome of the organism. Preferably the transgenic organism is a filamentous fungus, preferably of the genus Aspergillus, more preferably *Aspergillus niger.*

Therefore, the transgenic organism of the present invention includes an organism comprising any one of, or combinations of, the promoter according to the present invention, the nucleotide sequence coding for the enzyme according to the present invention, constructs according to the present invention, vectors according to the present invention, plasmids according to the present invention, cells according to the present invention, tissues according to the present invention or the products thereof. For example the transgenic organism can comprise a GOI, preferably an exogenous nucleotide sequence, under the control of the promoter according to the present invention. The transgenic organism can also comprise the nucleotide sequence coding for the enzyme of the present invention under the control of a promoter, which may be the promoter according to the present invention.

In a highly preferred embodiment, the transgenic organism does not comprise the combination of the promoter according to the present invention and the nucleotide sequence coding for the enzyme according to the present invention, wherein both the promoter and the nucleotide sequence are native to that organism and are in their natural environment. Thus, in these highly preferred embodiments, the present invention does not cover the native nucleotide coding sequence according to the present invention in its natural environment when it is under the control of its native promoter which is also in its natural environment. In addition, in this highly preferred embodiment, the present invention does not cover the native enzyme according to the present invention when it is in its natural environment and when it has been expressed by its native nucleotide coding sequence which is also in its natural environment and when that nucleotide sequence is under the control of its native promoter which is also in its natural environment.

The term "promoter" is used in the normal sense of the art, e.g. an RNA polymerase binding site in the Jacob-Mond theory of gene expression.

In one aspect, the promoter of the present invention is capable of expressing a GOI, which can be the nucleotide sequence coding for the enzyme of the present invention.

In another aspect, the nucleotide sequence according to the present invention is under the control of a promoter that allows expression of the nucleotide sequence. In this regard, the promoter need not necessarily be the same promoter as that of the present invention. In this aspect, the promoter may be a cell or tissue specific promoter. If, for example, the organism is a plant then the promoter can be one that affects expression of the nucleotide sequence in any one or more of stem, sprout, root and leaf tissues.

By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application No. 9421292.5 filed Oct. 21, 1994. That promoter comprises the sequence shown in FIG. 1.

Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994. That promoter comprises the sequence shown in FIG. 2.

Preferably, the promoter is the promoter of the present invention.

In addition to the nucleotide sequences described above, the promoters, particularly that of the present invention, could additionally include features to ensure or to increase expression in a suitable host. For example, the features can be conserved regions such as a Pribnow Box or a TATA box. The promoters may even contain other sequences to affect (such as to maintain, enhance, decrease) the levels of expression of the GOI. For example, suitable other sequences include the Shl-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

In addition the present invention also encompasses combinations of promoters and/or nucleotide sequences coding for proteins or enzymes and/or elements. For example, the present invention encompasses the combination of a promoter according to the present invention operatively linked to a GOI, which could be a nucleotide sequence according to the present invention, and another promoter such as a tissue specific promoter operatively linked to the same or a different GOI.

The present invention also encompasses the use of promoters to express a nucleotide sequence coding for the enzyme according to the present invention, wherein a part of the promoter is inactivated but wherein the promoter can still function as a promoter. Partial inactivation of a promoter in some instances is advantageous.

In particular, with the Amy 351 promoter mentioned earlier it is possible to inactivate a part of it so that the partially inactivated promoter expresses GOIs in a more specific manner such as in just one specific tissue type or organ.

The term "inactivated" means partial inactivation in the sense that the expression pattern of the promoter is modified but wherein the partially inactivated promoter still functions as a promoter. However, as mentioned above, the modified promoter is capable of expressing a GOI in at least one (but not all) specific tissue of the original promoter. One such promoter is the Amy 351 promoter described above.

Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part.

Another modification is to mutate the binding sites for regulatory proteins for example the CreA protein known from filamentous fungi to exert carbon catabolite repression, and thus abolish the catabolite repression of the native promoter.

The term "GOI" with reference to the present invention means any gene of interest. A GOI can be any nucleotide that is either foreign or natural to the organism (e.g. filamentous fungus, preferably of the genus Aspergillus, or a plant) in question. Typical examples of a GOI include genes encoding for proteins and enzymes that modify metabolic and catabolic processes. The GOI may code for an agent for introducing or increasing pathogen resistance. The GOI may even be an antisense construct for modifying the expression of natural transcripts present in the relevant tissues. The GOI may even code for a non-natural protein of a filamentous fungus, preferably of the genus Aspergillus, or a compound that is of benefit to animals or humans.

For example, the GOI could code for a pharmaceutically active protein or enzyme such as any one of the therapeutic compounds insulin, interferon, human serum albumin, human growth factor and blood clotting factors. In this regard, the transformed cell or organism could prepare acceptable quantities of the desired compound which would be easily retrievable from, the cell or organism. The GOI may even be a protein giving nutritional value to a food or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as chymosin, thaumatin and α-galactosidase. The GOI can be a gene encoding for any one of a pest toxin, an antisense transcript such as that for patatin or α-amylase, ADP-glucose pyrophosphorylase (e.g. see EP-A-0455316), a protease antisense or a glucanase.

The GOI can be the nucleotide sequence coding for the α-amylase enzyme which is the subject of our co-pending UK patent application 9413439.2 filed on Jul. 4, 1994, the sequence of which is shown in FIG. 3. The GOI can be the nucleotide sequence coding for the α-amylase enzyme which is the subject of our co-pending UK patent application 9421290.9 filed on Oct. 21, 1994, the sequence of which is shown in FIG. 4. The GOI can be any of the nucleotide sequences coding for the ADP-glucose pyrophosphorylase enzymes which are the subject of our co-pending PCT patent application PCT/EP94/01082 filed Apr. 7, 1994, the sequences of which are shown in FIGS. 5 and 6. The GOI can be any of the nucleotide sequences coding for the α-glucan lyase enzyme which are described in our co-pending PCT patent application PCT/EP94/03397 filed Oct. 15, 1994, the sequences of which are shown in FIGS. 7–10.

In one preferred embodiment, the GOI is a nucleotide sequence coding for the enzyme according to the present invention.

As mentioned above, a preferred host organism is of the genus Aspergillus, such as *Aspergillus niger.*

The transgenic Aspergillus according to the present invention can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R. (Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In : Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghorn J. R. (Editors) Aspergillus: 50 years on. Progress in industrial microbiology vol 29.

Elsevier Amsterdam 1994. pp. 641–666). However, the following commentary provides a summary of those teachings for producing transgenic Aspergillus according to the present invention.

Filamentous fungi have during almost a century been widely used in industry for production of organic compounds and enzymes. Traditional japanese koji and soy fermentations have used Aspergillus sp. for hundreds of years. In this century *Aspergillus niger* has been used for production of organic acids particular citric acid and for production of various enzymes for use in industry.

There are two major reasons for that filamentous fungi have been so widely used in industry. First filamentous fungi can produce high amounts of extracellular products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic Aspergillus, expression constructs are prepared by inserting a GOI (such as an amylase or SEQ. I.D. No. 2) into a construct designed for expression in filamentous fungi.

Several types of constructs used for heterologous expression have been developed. The constructs contain the promoter according to the present invention (or if desired another promoter if the GOI codes for the enzyme according to the present invention) which is active in fungi. Examples of promoters other than that of the present invention include a fungal promoter for a highly expressed extracellulary enzyme, such as the glucoamylase promoter or the $\alpha$-amylase promoter. The GOI can be fused to a signal sequence (such as that of the present invention or another suitable sequence) which directs the protein encoded by the GOI to be secreted. Usually a signal sequence of fungal origin is used, such as that of the present invention. A terminator active in fungi ends the expression system, such as that of the present invention.

Another type of expression system has been developed in fungi where the GOI is fused to a smaller or a larger part of a fungal gene encoding a stable protein. This can stabilize the protein encoded by the GOI. In such a system a cleavage site, recognized by a specific protease, can be introduced between the fungal protein and the protein encoded by the GOI, so the produced fusion protein can be cleaved at this position by the specific protease thus liberating the protein encoded by the GOI ("POI"). By way of example, one can introduce a site which is recognized by a KEX-2 like peptidase found in at least some Aspergilli. Such a fusion leads to cleavage in vivo resulting in protection of the POI and production of POI and not a larger fusion protein.

Heterologous expression in Aspergillus has been reported for several genes coding for bacterial, fungal, vertebrate and plant proteins. The proteins can be deposited intracellularly if the GOI is not fused to a signal sequence. Such proteins will accumulate in the cytoplasm and will usually not be glycosylated which can be an advantage for some bacterial proteins. If the GOI is equipped with a signal sequence the protein will accumulate extracellulary.

With regard to product stability and host strain modifications, some heterologous proteins are not very stable when they are secreted into the culture fluid of fungi. Most fungi produce several extracellular proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A very common used transformation marker is the amdS gene of *A. nidulans* which in high copy number allows the fungus to grow with acrylamide as the sole nitrogen source.

Even though the enzyme, the nucleotide sequence coding for same and the promoter of the present invention are not disclosed in EP-B-0470145 and CA-A-2006454, those two documents do provide some useful background commentary on the types of techniques that may be employed to put the present invention into practice. Some of these background teachings are now included in the following commentary.

The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system.

A review of the general techniques may be found in articles by Potrykus (Annu Rev Plant Physiol Plant Mol Biol [1991] 42:205–225) and Christou (Agro-Food-Industry Hi-Tech Mar./Apr. 17–27, 1994).

Thus, in one aspect, the present invention relates to a vector system which carries a promoter or nucleotide sequence or construct according to the present invention and which is capable of introducing the promoter or nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The promoter or nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct.

Furthermore, the vector system is preferably an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the promoter or nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable Agrobacterium strain, e.g. *Agrobacterium tumefaciens*. The Ti-plasmid harbouring the promoter or nucleotide sequence or construct of the invention is thus preferably transferred into a suitable Agrobacterium strain, e.g. *A. tumefaciens*, so as to obtain an Agrobacterium cell harbouring the promoter or nucleotide sequence or construct of the invention, which DNA is subsequently transferred into the plant cell to be modified.

As reported in CA-A-2006454, a large amount of cloning vectors are available which contain a replication system in *E. coli* and a marker which allows a selection of the transformed cells. The vectors contain for example pBR 322, pUC series, M13 mp series, pACYC 184 etc. In such a way, the nucleotide or construct or promoter of the present invention can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the-next DNA sequence. Each sequence can be cloned in the same or different plasmid. After each introduction method of the desired promoter or construct or nucleotide sequence according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech Mar./Apr. 17–27, 1994). With this technique, infection of a plant may be done on a certain part or tissue of the plant, i.e. on a part of a leaf, a root, a stem or another part of the plant.

Typically, with direct infection of plant tissues by Agrobacterium carrying the promoter and/or the GOI, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

In summation, the present invention provides a glucanase enzyme and the nucleotide sequence coding for the same. In addition, it provides a promoter that can control the expression of that, or another, nucleotide sequence. In addition it includes terminator and signal sequences for the same.

The following sample was deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Jan. 16, 1995:

*E. coli* containing plasmid pEGLA-3 {i.e. *E. coli* DH5α-pEGLA-3}. The deposit number is NCIMB 40704.

The present invention will now be described by way of example.

BRIEF DESCRIPTION OF THE DRAWINGS

In the following Examples reference is made to the accompanying Figures in which FIGS. 1–10 are sequences of promoters and GOIs of earlier patent applications that are useful for use with the aspects of the present invention;

EXAMPLES

Figure 11:
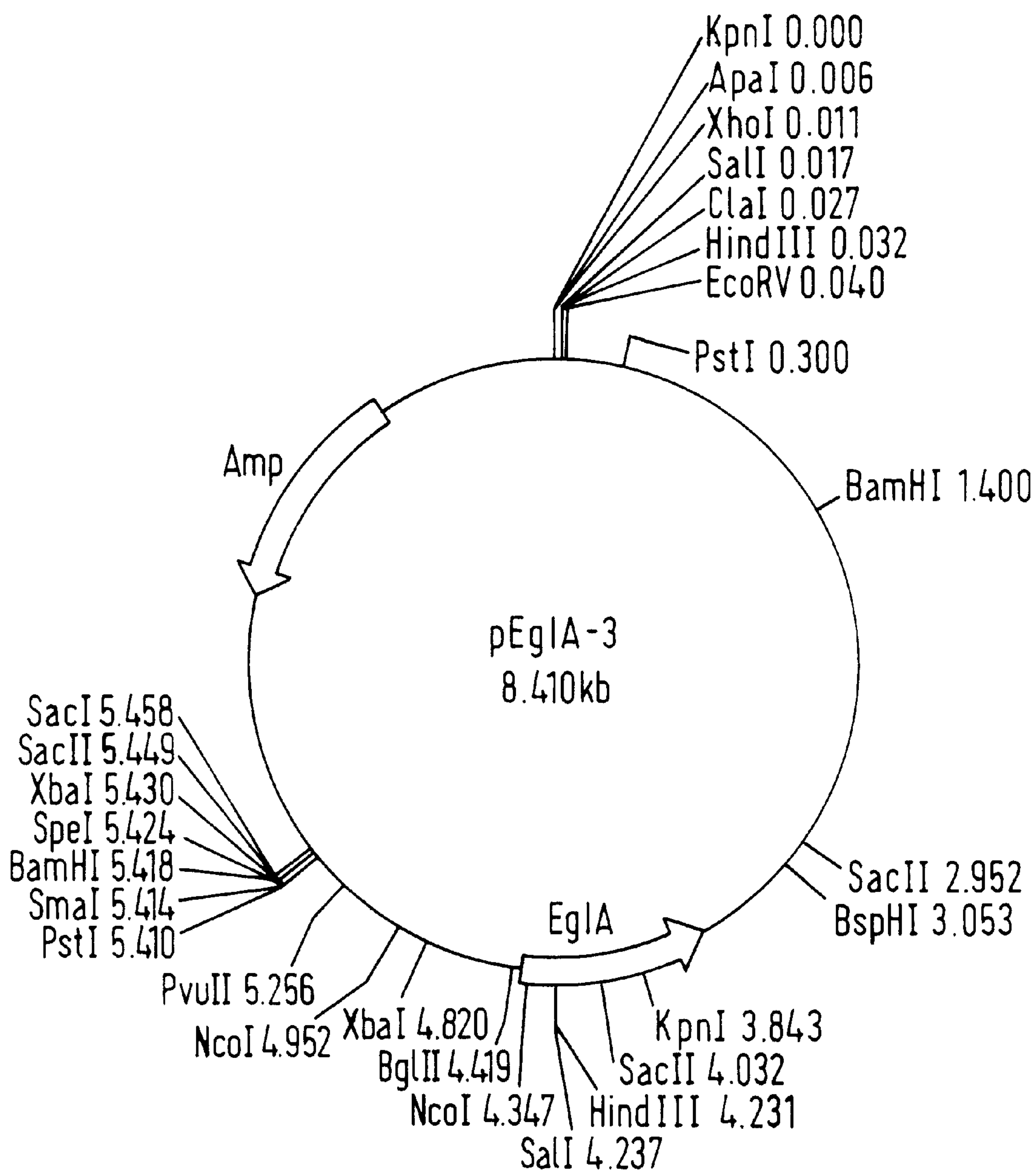
FIG. 11 is a plasmid map of plasmid pEGLA-3.

The following Examples discuss recombinant DNA techniques. General teachings of recombinant DNA techniques may be found in Sambrook, J., Fritsch, E. F., Maniatis T. (Editors) Molecular Cloning. A laboratory manual. Second edition. Cold Spring Harbour Laboratory Press. New York 1989.

Purification of the β-glucanase

*Aspergillus niger* 3M43 was grown in medium containing wheat bran and beet pulp. The fermentation broth was separated from the solid part of the broth by filtration. Concentrated fermentation broth was then loaded on a 25×100 mm Q-SEPHAROSE (Pharmacia) high Performance column, equilibrated with 20 mM Tris, HCl pH 7.5, and a linear gradient from 0–500 mM NaCl was performed and fractions of the eluate was collected. The β-glucanase eluted at ca 100 mM NaCl. The fractions containing glucanase were combined and desalted using a 50×200 mm G-25 SEPHAROSE Superfine (Pharmacia). The column was then eluted with distilled water. After desalting the enzyme was concentrated using High-Trap spin columns.

Next the concentrated and desalted fractions were subjected to gel filtration on a 50×600 mm SUPERDEX 50 column. The sample was loaded and the column was eluted with 0.2 M Phosphate buffer pH 7.0 plus 0.2 M NaCl, and fractions of the eluate were collected. The fractions containing glucanase were combined and desalted and concentrated as described above.

The combined fractions were loaded on a 16×100 mm PhenylSEPHAROSE High Performance column (Pharmacia), equilibrated with 50 mM Phosphate buffer pH⁻6.0, containing 1.5 M $(NH_4)_2SO_4$. A gradient where the $(NH_4)_2SO_4$ concentration was varied from 1.5–0 M was applied and the eluate collected in fractions. The fractions containing glucanase were combined. The purity of the β-1,4-glucanase was evaluated SDS-PAGE using the Phast system gel (Pharmacia).

Characterization

The molecular weight of the purified glucanase was determined by mass spectrometry using laser desorption technology. The MW of the glucanase was found to be 24,235 D±50 D.

The pI value was determined by use of a Broad pI Kit (Pharmacia). The glucanase has a pI value of about 4.

After SDS-PAGE analysis, treatment PAS reagent showed that the glucanase is not glycosylated. The PAS staining was done according to the procedure of I. Van-Seuningen and M. Davril (1992) Electrophoresis 13 pp 97–99.

Amino Acid Sequencing of the β-glucanase

The enzyme was digested with endoproteinase Lys-C sequencing grade from Boehringer Mannheim using a modification of the method described by Stone & Williams 1993 (Stone, K. L. and Williams, K. R. (1993). Enzymatic digestion of Proteins and HPLC Peptide Isolation. In: Matsudaira P. (Editor). A practical Guide to Protein and Peptide Purification for Microsequencing. Second Edition. Academic Press, San Diego 1993. pp 45–73).

Freeze dried β-glucanase (0.4 mg) was dissolved in 50 μl of 8M urea, 0.4 M $NH_4HCO_3$, pH 8.4. After overlay with $N_2$ and addition of 5 μl of 45 mM DTT, the protein was denatured and reduced for 15 min at 50° C. under $N_2$. After cooling to RT, 5 μl of 100 mM iodoacetamide was added for the cysteines to be derivatised for 15 min at RT in the dark under $N_2$. Subsequently, 90 μl of water and 5 μg of endoproteinase Lys-C in 50 μl of 50 mM Tricine and 10 mM EDTA, pH 8.0, was added and the digestion was carried out for 24 h at 37° C. under $N_2$. The resulting peptides were separated by reversed phase HPLC on a VYDAC C18 column (0.46×15 cm; 10 μm; The Separations Group; California) using solvent A: 0.1% TFA in water and solvent B: 0.1% TFA in acetonitrile. Selected peptides were rechromatographed on a Develosil C18 column (0.46×10 cm; 3 μm) using the same solvent system prior to sequencing on an Applied Biosystems 476A sequencer using pulsed-liquid fast cycles.

The following peptide sequences were found:

SEQ I.D. No. 4

SEQ I.D. No. 5

SEQ I.D. No. 6

SEQ I.D. No. 7

SEQ I.D. No. 8

Isolation of a PCR Clone of a Fragment of the Gene

PCR primers were synthesised using an Applied Biosystems DNA synthesiser model 392. In this regard, PCR primers were synthesized from two of the found peptide sequences, WEVWYGT from Seq I.D. No. 4 and WTWSGG from Seq I.D. No. 7. The primer derived from WEVWYGT (reversed) is shown as Seq I.D. No. 9 and the primer derived from WTWSGG is shown as Seq I.D. No. 10—see below:

SEQ. I.D. No. 10

TGG ACN TGG WSN GGN GG 17 mer 256 mixture

SEQ. I.D. No. 9

CTN CCR TAC CAN ACY TCC CA 20 mer 64 mixture

PCR amplification was performed with 100 pmol of each of these primers in 100 μl reactions using the Amplitaq II kit (Perkin Elmer). The program was:

| STEP | TEMP | TIME |
|---|---|---|
| 1 | 94° C. | 2 min |
| 2 | 94° C. | 1 min |
| 3 | 55° C. | 2 min |
| 4 | 72° C. | 2 min |
| 5 | 72° C. | 5 min |
| 6 | 5° C. | SOAK |

Steps 2–4 were repeated for 40 cycles.

The program was run on a PERKIN ELMER DNA Thermal Cycler.

A 350 bp amplified fragment was isolated and cloned into a pT7-Blue T-vector according to the manufacturer's instructions (Novagen). A fragment was isolated and sequenced. The found sequence showed that it was indeed a part of the glucanase gene.

Isolation of *A. niger* Genomic DNA 1 g. of frozen *A. niger* mycelium was ground in a mortar under liquid nitrogen. Following evaporation of the nitrogen cover, the ground mycelium was extracted with 15 ml of an extraction buffer (100 mM Tris-HCl, pH 8.0, 0.50 mM EDTA, 500 mM NaCl, 10 mM β-mercaptoethanol) containing 1 ml 20% sodium dodecyl sulphate. After incubation at 65° C. for 10 min. 5 ml 5M KAc. pH 5.0, was added and the mixture further incubated, after mixing, on ice for 20 mins. The mixture was then centrifuged for 20 mins. and the supernatant mixed with 0.6 vol. isopropanol to precipitate the extracted DNA. After further centrifugation for 15 mins. the DNA pellet was dissolved in 0.7 ml TE (10 mM Tris, HCl pH 8.0, 1 mM EDTA) and precipitated with 75 μl 3M NaAc, pH 4.8, and 500 μl isopropanol. After centrifugation the pellet was washed with 70% ETOH and dried under vacuum. The DNA was dissolved in 200 μl TE and stored at −20° C.

Construction of a Library

20 μg genomic DNA was partly digested with Tsp509I, which gives ends which are compatible with EcoRI ends. The digested DNA was separated on a 1% agarose gel and fragments of 4–10 kb was purified. A λZAPII EcoRI/CIAP kit from Stratagene was used for library construction according to the manufacturers instructions. 2 μl of the ligation (totally 5 μl) was packed with Gigapack Gold II packing extract according to the manufacturer's instuctions (Stratagene). The library contained 650.000 independent clones.

Screening of the Library

2×50,000 pfu was plated on NZY plates (5 g NaCl, 2 mg $MgSO_4$, $7H_2O$, 5 g yeast extract, 10 g casein hydrolysate, 15 g agar per liter) and plaquelifts were done on Hybond N sheets (Amersham). The sheets were hybridized with the PCR clone labelled with $^{32}P$ dCTP (Amersham) using Ready-to-go labelling kit from Pharmacia. The plaquelifts and hybridization were done in duplicate and positive clones were reckoned only when hybridization could be detected on both sheets. The nucleotide sequence of the present invention was sequenced using a ALF-laser fluorescence sequencer (Pharrnacia). The sequence contained all the found amino acid sequence, confirming that the isolated gene indeed encoded the β-1,4-endoglucanase.

Sequence Information

SEQ. ID. Nos. 12 and 13 presents the promoter sequence, the enzyme coding sequence, the terminator sequence and the signal sequence and the amino acid sequence of the enzyme of the present invention.

Testing Enzyme Activity

The purified protein was assayed for endo β-1,4 glucanase activity using Azurine-crosslinked barley β-glucan tablet (trade name: Glucazyme tablets supplied by Megazyme, Australia) by the instructions given by the manufacturer.

The purified enzyme gave a high activity on this substrate. Typically the enzyme has a specific activity of 2250 micromol glucose per min per mg of protein.

Induction of the Eg1A Gene: Identification of Inducing Carbon Source

The Table below shows the identification of a number of high and low mole cular weight inducers of the glucanase promoter. This analysis was carried out using the full length glucanase promoter of the present invention fused to the *E coli* β-glucuronidase gene.

The inducing strength of different carbon sources was determined quantitatively by measuring the intracellular GUS specific activity to hydrolyse p-nitrophenol glucuronide.

| CARBON SOURCE (1%) | GUS ACTIVITY (units/mg)- 24 hours |
|---|---|
| xylose | 12.91 |
| xylitol | 10.62 |
| arabinose | 8.50 |
| arabitol | 14.40 |
| glucose | 20.25 |
| cellubiose | 19.44 |
| xylo-oligomer 70 | 11.80 |
| glucopyranoside | 19.70 |
| methyl-xylopyranoside | 12.60 |
| xyloglucan | 13.90 |
| pectin | 9.70 |
| arabinogalactan | 30.20 |
| arabitol + glucose | 29.50 |

Surprisingly glucose, which is normally a potent catabolite repressor, induces the glucanase promoter.

Accordingly, the present invention also relates to a promoter that is inducible by glucose.

In addition, the present invention relates to the use of glucose to induce a promoter.

These aspects of the present invention are different to the teachings of WO 94/04673 which discloses a fungal promoter that is active in the presence of glucose. In this regard, the promoter of the present invention is not only active in the presence of glucose but that it is also inducible by glucose.

One of the advantages of having a glucanase promoter that is inducible by glucose is that the promoter can be used to express a GOI, and thereby be used to prepare a POI (such as an heterologous POI), in a glucose containing environment. This is important because glucose is one of preferred carbon sources for biomass accumulation. In addition, glucose containing media are expected to produce lower amounts of proteases, thereby providing better yields of the POI. In addition, the use of a derepressed promoter in a derepressed host strain will increase the speed and efficiency of reaction media, such as a fermentation reaction medium. In addition, the use of mixed carbon sources during fermentation will allow the efficient induction of this promoter, for example at low levels of glucose and a cheap carbon source (e.g. sugar beet pulp).

Figure 12:
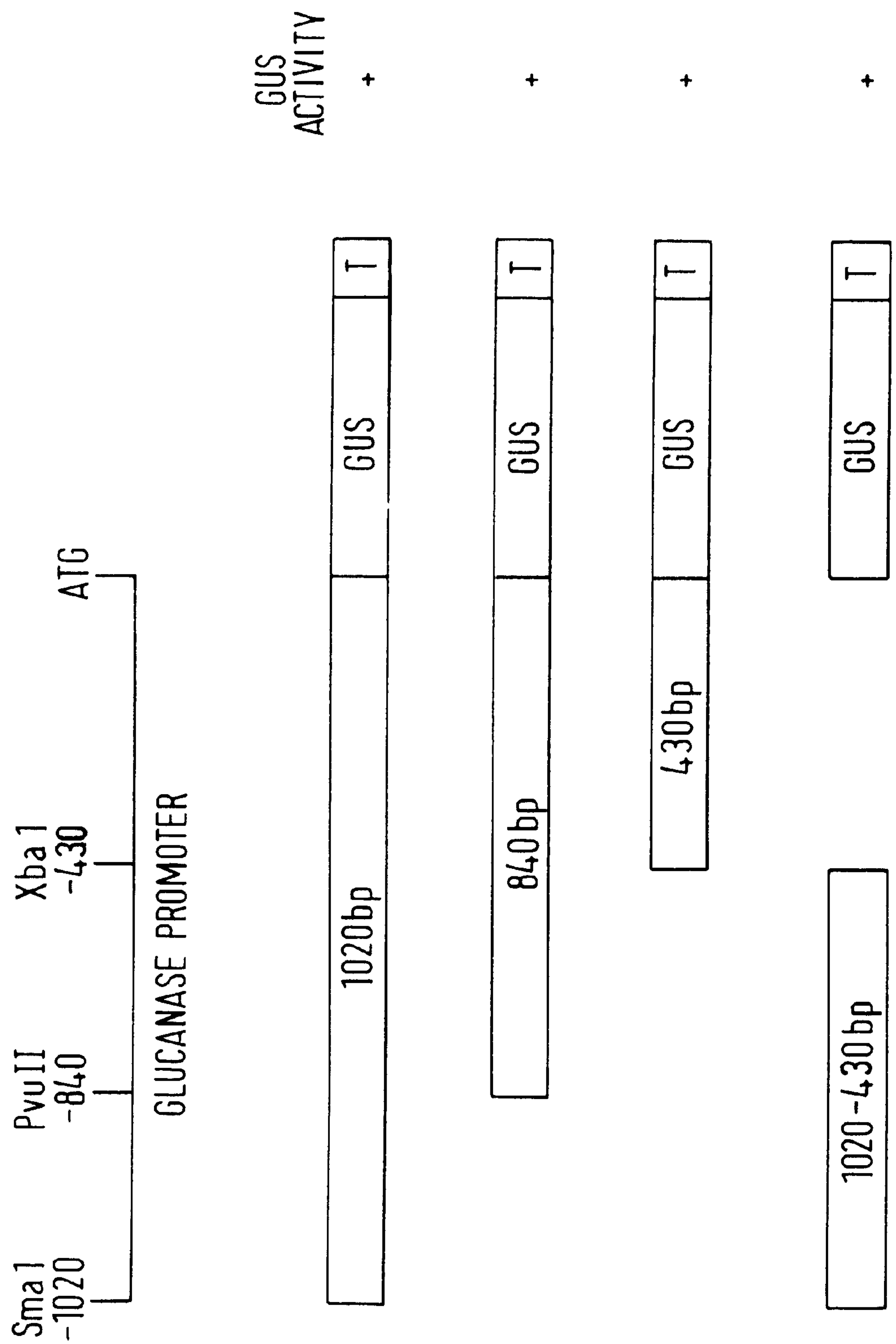
FIG. 12 is a schematic diagram of some promoter deletions.

Effects of Promoter Deletions on the Regulation of the Expression of the Glucanase Gene A series of deletion studies, which are shown in FIG. 12, were performed. In these studies, the different promoter deletion constructs shown in FIG. 12 were fused to the GUS gene. The activity of the reporter gene was assayed qualitatively. The results showed that none of the deletions abolished the inducibility of the glucanase promoter. These results indicate the presence of multiple sites for transcriptional activation and initiation of transcription.

HETEROLOGOUS PROTEIN PRODUCTION USING TRANSFORMANTS OF ASPERGILLUS NIGER COMPRISING THE GLUCANASE PROMOTER (GP) AND THE GLUCANASE SIGNAL SEQUENCE (Gss)

Transformation of *Asperillus Niger*

The protocol for transformation of *A. niger* was based on the teachings of Buxton, F. P., Gwynne D. I., Davis, R. W. 1985 (Transformation of *Aspergillus niger* using the argB gene of *Aspergillus nidulans*. Gene 37:207–214), Daboussi, M. J., Djeballi, A., Gerlinger, C., Blaiseau, P. L., Cassan, M., Lebrun, M. H., Parisot, D., Brygoo, Y. 1989 (Transformation of seven species of filamentous fungi using the nitrate reductase gene of *Aspergillus nidulans*, Curr. Genet. 15:453–456) and Punt, P. J., van den Hondel, C. A. M. J. J. 1992 (Transformation of filamentous fungi based on hygromycin B and Phleomycin resistance markers. Meth. Enzym. 216:447–457).

For the purification of protoplasts, spores from one PDA (Potato Dextrose Agar—from Difco Lab. Detroit) plate of fresh sporulated N400 (CBS 120.49, Centraalbureau voor Schimmelcultures, Baarn) (7 days old) are washed off in 5–10 ml water. A shake flask with 200 ml Potato Dextrose Broth (difco 0549-17-9, Difco Lab. Detroit) is inoculated with this spore suspension and shaken (250 rpm) for 16–20 hours at 30° C.

The mycelium is harvested using Miracloth paper and 3–4 g wet mycelium are transferred to a sterile petri dish with 10 ml STC (1.2 M sorbitol, 10 mM Tris HCl pH 7,5, 50-mM $CaCl_2$) with 75 mg lysing enzymes (Sigma L-2265) and 4500 units lyticase (Sigma L-8012).

The mycelium is incubated with the enzyme until the mycelium is degraded and the protoplasts are released. The degraded mycelium is then filtered through a sterile 60 μm mesh filter. The protoplasts are harvested by centrifugation 10 min at 2000 rpm in a swing out rotor. The supernatant is discarded and the pellet is dissolved in 8 ml 1.5 M $MgSO_4$ and then centrifuged at 3000 rpm for 10 min.

The upper band, containing the protoplasts is transferred to another tube, using a transfer pipette and 2 ml 0.6 M KCl is added. Carefully 5 ml 30% sucrose is added on the top and the tube is centrifuged 15 min at 3000 rpm.

The protoplasts, lying in the interface band, are transferred to a new tube and diluted with 1 vol. STC. The solution is centrifuged 10 min at 3000 rpm. The pellet is washed twice with STC, and finally solubilized in 1 ml STC. The protoplasts are counted and eventually concentrated before transformation.

For the transformation, 100 μl protoplast solution ($10^6$–$10^7$ protoplasts) are mixed with 10 μl DNA solution containing 5–10 μg DNA and incubated 25 min at room temperature. Then 60% PEG-4000 is carefully added in portions of 200 μl, 200 μl and 800 μl. The mixture is incubated 20 min at room temperature. 3 ml STC is added to the mixture and carefully mixed. The mixture is centrifugated 3000 rpm for 10 min.

The supernatant is removed and the protoplasts are solubilized in the remaining of the supernatant. 3–5 ml topagarose is added and the protoplasts are quickly spread on selective plates.

Glucanase Promoter and Heterologous Gene Expression

Figure 13:
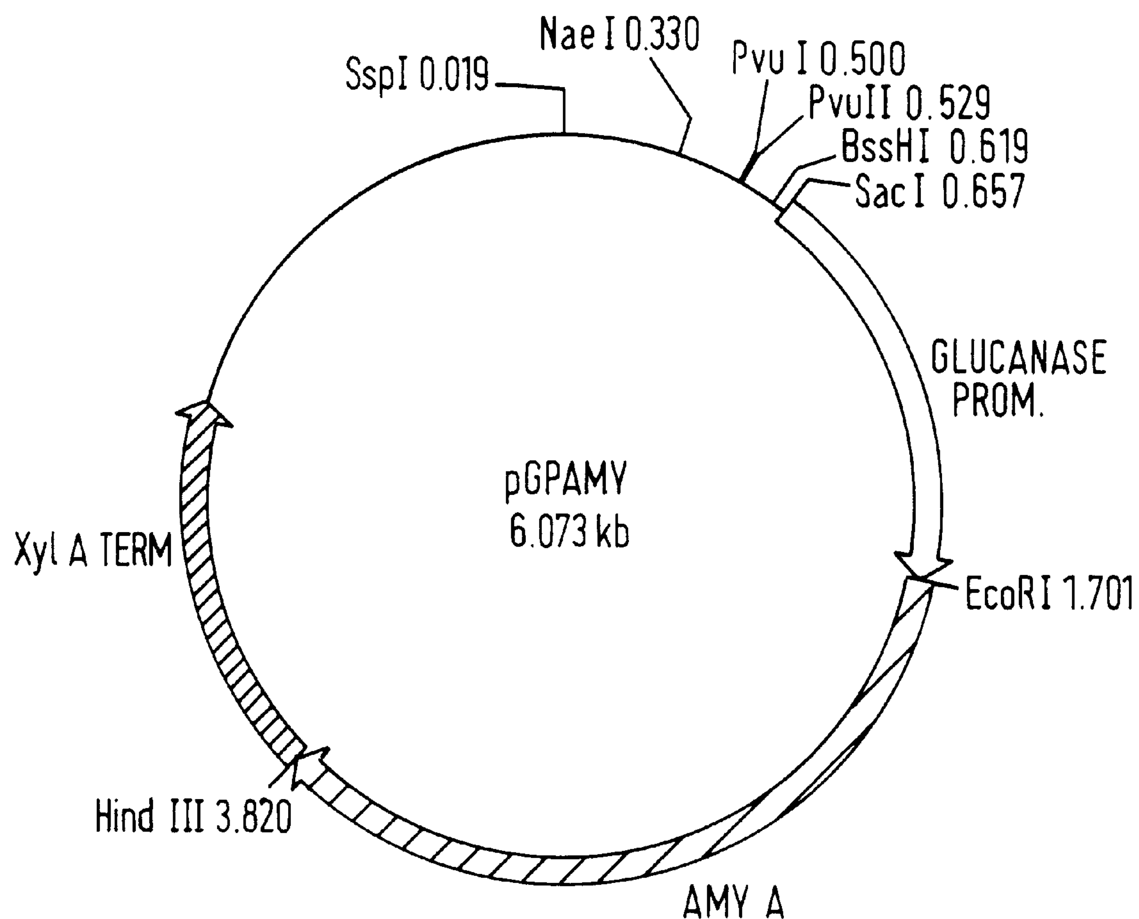
FIG. 13 is a plasmid map of pGPAMY.

FIG. 13 shows the expression vector pGPAmy that was used in these studies. This expression vector comprises the glucanase promoter fused to the *Thermomyces lanuginosus* precursor form of the α-amylase gene. Transcription from the promoter is terminated using the xylanase A terminator. This construct was used in a co-transformation experiment with the hygromycin resistance gene as the selectable marker.

Figure 14:
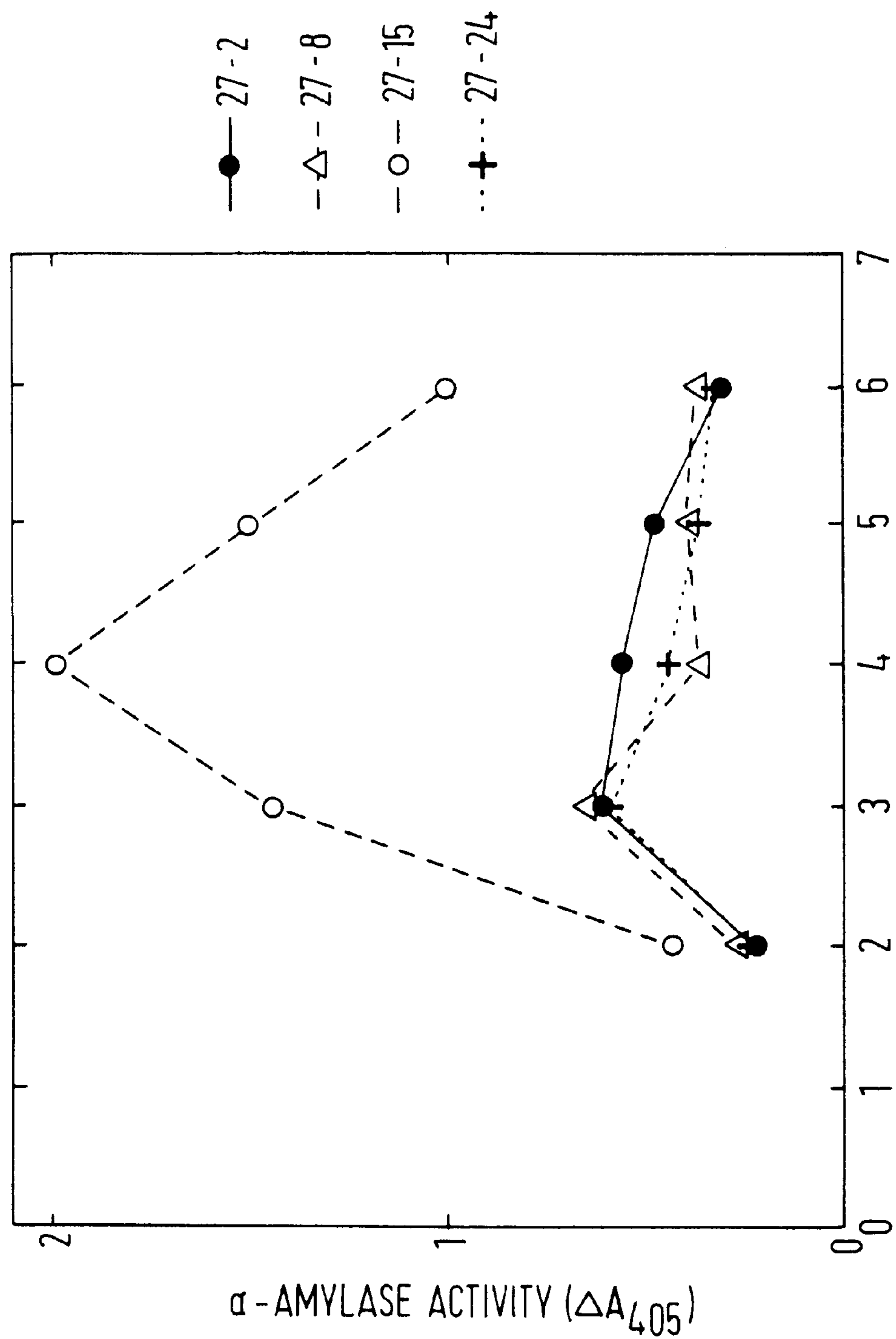
FIG. 14 is a graph.

The production of α-amylase using four independent transformants containing the expression vector pGPAmy when grown on sugar beet pulp and wheat bran is shown in FIG. 14. The α-amylase activity was first detected in the culture medium after 48 hours of growth. A peak of enzyme activity was observed after days 3 and 4.

Glucanase Signal Sequence & Heterologous Protein Production

For these studies, the expression vector pGPGssAmyHya was used.

Figure 15:
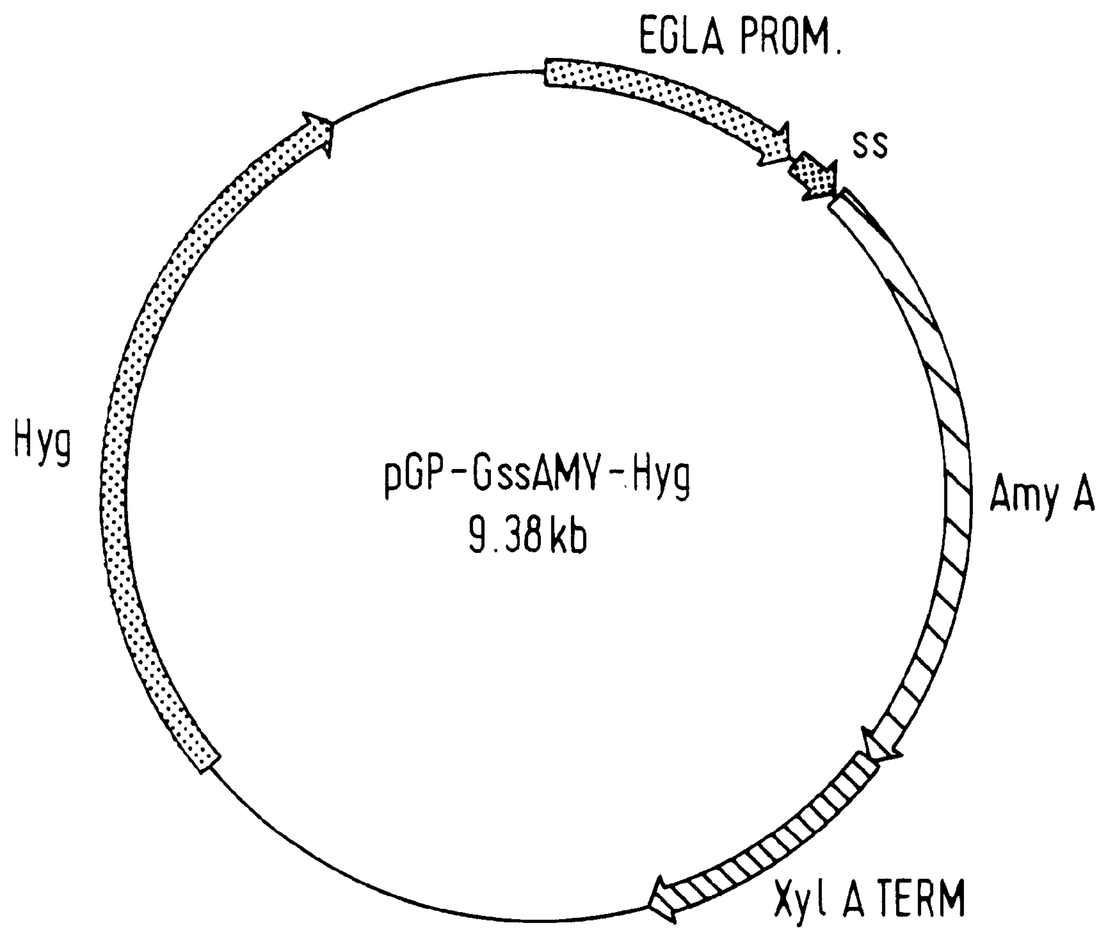
FIG. 15 is a plasmid map of pGP-GssAMY-Hyg.

The vector pGPGssAmyHyg is shown in FIG. 15. This vector comprises the mature α-amylase gene translationally fused to the glucanase signal peptide (labelled ss). In addition, this vector comprises the promoter of the present invention (labelled EG1.A) and the xylanase A terminator. Transcription from this vector is therefore under the control of the glucanase promoter and termination by the xylanase A terminator.

This construct was used to test inter alia the efficiency of the signal peptide in heterologous protein secretion.

Figure 16:
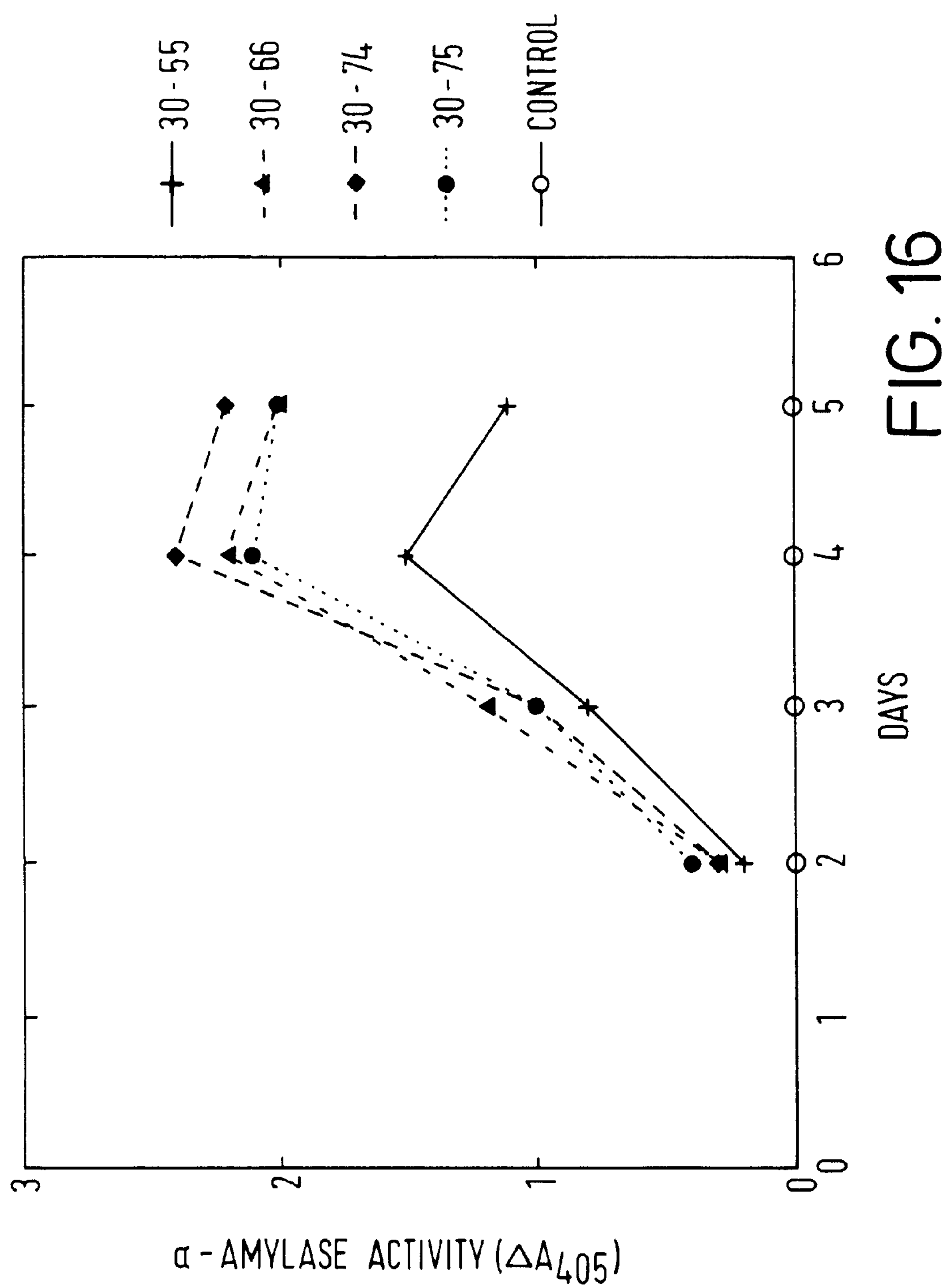
FIG. 16 is a graph.

FIG. 16 shows the results of the induction of α-amylase by use of the construct in strain 6M179 when grown in sugar beet pulp/wheat bran. The results show that the enzyme activity was localised in the culture medium and was first detected after 48 hours of growth. Accumulation of enzyme activity was observed at day 4.

Western Blot

Figure 17:
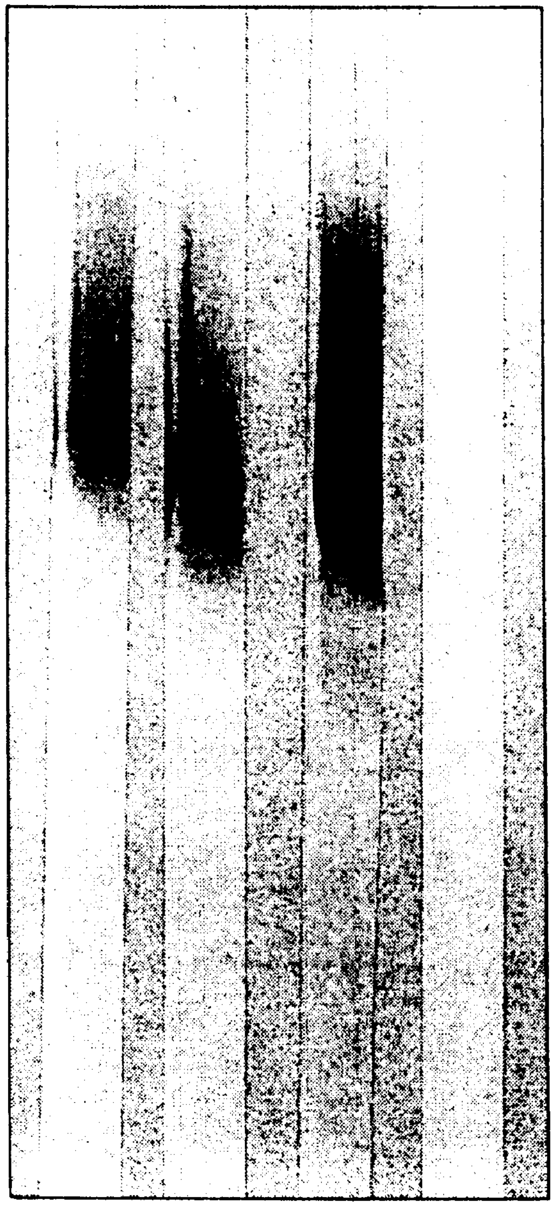
FIG. 17 is a Western Blot of proteins from the supernatant of three independent transformants separated by SDS-PAGE and blotted to a membrane.

FIG. 17 shows a Western blot of proteins from the supernatant of three independent transformants separated by SDS-PAGE and blotted to a membrane. A synthetic peptide with 15 amino acid residues of *T lanuginosus* α-amylase recognised a single band on Western blots of culture supernatants from the transformants.

Antibody Production

Antibodies were raised against the enzyme of the present invention by injecting rabbits with the purified enzyme and isolating the immunoglobulins from antiserum according to procedures described according to N Harboe and A Ingild ("Immunization, Isolation of Immunoglobulins, Estimation of Antibody Titre" In A Manual of Quantitative Immunoelectrophoresis, Methods and Applications, N H Axelsen, et al (eds.), Universitetsforlaget, Oslo, 1973) and by T G Cooper ("The Tools of Biochemistry", John Wiley & Sons, New York, 1977).

SUMMARY

Even though it is known that *Aspergillus niger* produces several enzvmes which can degrade β-glucan, the present invention provides a novel and inventive β-1,4-endoglucanase, as well as the coding sequence therefor, the termination sequence therefor, the signal sequence therefor, and the promoter for those sequences. An important advantage of the present invention is that the enzyme can be produced in high amounts. In addition, the promoter and the regulatory sequences (such as the signal sequence and the terminator) can be used to express or can be used in the expression of GOIs in organisms, such as in *A. niger.*

The enzyme of the present invention is advantageous for feed supplements. In addition, it can be used in the brewing industry as it has a high fibre-conversion potential. In addition, there are fewer processing problems when the enzyme is used, particularly with non-starchy polysaccharides. In addition, the enzyme efficiently degrades β-glucans, therefore it can be used advantageously in the brewing industry to lower viscosity and also improve the filterability of beer. This is important as large molecular weight glucans in beer and the like can cause filtration difficulties and give rise to sediments, gels and hazes.

The signal sequence of the present invention is useful for secretion of a POI, such as a heterologous POI, thereby improving the quality and quantity of the POI.

Other modifications of the present invention will be apparent to those skilled in the art without departing from the scope of the invention.

What is claimed is:

1. An isolated glucanase enzyme having the sequence shown as SEQ ID NO: 1.

2. An isolated glucanase enzyme coded for by a nucleic acid molecule having the nucleotide sequence shown as SEQ ID NO:2.

3. An isolated nucleic acid molecule coding for the glucanase enzyme according to claim 1.

4. An isolated nucleic acid molecule having the sequence shown as SEQ ID NO:2.

5. A method of degrading a glucan polymer comprising adding the glucanase enzyme of claim 1 to the glucan polymer.

6. The method of claim 5 further comprising determining the extent of glucan polymer degradation.

7. A method of degrading a glucan polymer comprising adding the glucanase enzyme of claim 2 to the glucan polymer.

8. The method of claim 7 further comprising determining the extent of glucan polymer degradation.

9. The isolated nucleic acid molecule of claim 3, operatively linked to a promoter.

10. The isolated nucleic acid molecule of claim 4 operatively linked to a promoter.

11. A construct or vector comprising or expressing the isolated nucleic acid molecule of claim 3.

12. A construct or vector comprising or expressing the isolated nucleic acid molecule of claim 4.

13. A plasmid comprising or expressing the isolated nucleic acid molecule of claim 3.

14. A plasmid comprising or expressing the isolated nucleic acid molecule of claim 4.

15. A process for preparing a glucanase enzyme according to claim 1 comprising expressing a nucleic acid molecule having the nucleotide sequence shown as SEQ ID NO:2.

16. A process for preparing a glucanase enzyme comprising expressing the isolated nucleic acid molecule of claim 3.

* * * * *